(12) United States Patent
Jeon et al.

(10) Patent No.: US 9,617,520 B2
(45) Date of Patent: Apr. 11, 2017

(54) DEVICE AND METHOD OF 3-DIMENSIONALLY GENERATING IN VITRO BLOOD VESSELS

(71) Applicant: SNU R&DB FOUNDATION, Seoul (KR)

(72) Inventors: Noo Li Jeon, Seoul (KR); Ju Hun Yeon, Gyeongsangnam-do (KR); Qing Ping Hu, Seongnam-si (KR); Sudong Kim, Seoul (KR); Hyun Jae Lee, Gyeonggi-do (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 14/855,513

(22) Filed: Sep. 16, 2015

(65) Prior Publication Data

US 2016/0102293 A1    Apr. 14, 2016

Related U.S. Application Data

(60) Division of application No. 13/089,130, filed on Apr. 18, 2011, now abandoned, which is a continuation-in-part of application No. 11/849,194, filed on Aug. 31, 2007, now Pat. No. 7,947,491.

(60) Provisional application No. 60/841,721, filed on Aug. 31, 2006, provisional application No. 60/841,798, filed on Aug. 31, 2006.

(51) Int. Cl.
| | |
|---|---|
| *C12N 5/071* | (2010.01) |
| *B01D 9/00* | (2006.01) |
| *C12M 3/00* | (2006.01) |
| *C12M 1/12* | (2006.01) |
| *C12M 1/00* | (2006.01) |

(52) U.S. Cl.
CPC .......... *C12N 5/0691* (2013.01); *B01D 9/0054* (2013.01); *C12M 21/08* (2013.01); *C12M 25/14* (2013.01); *C12M 29/10* (2013.01); *C12N 2501/40* (2013.01); *C12N 2533/70* (2013.01); *C12N 2533/90* (2013.01)

(58) Field of Classification Search
CPC ...... C12M 21/08; C12M 25/14; C12M 29/10; B01D 9/0054; C12N 2501/40; C12N 2533/70; C12N 2533/90; C12N 5/0691
USPC ...................................................... 435/288.5
See application file for complete search history.

(56) References Cited

U.S. PATENT DOCUMENTS

| | | |
|---|---|---|
| 7,141,429 B2 | 11/2006 | Munson et al. |
| 2004/0106129 A1 | 6/2004 | Crook et al. |
| 2004/0121066 A1 | 6/2004 | Anderson et al. |
| 2005/0217750 A1 | 10/2005 | Jeon et al. |
| 2005/0266582 A1 | 12/2005 | Modlin et al. |

(Continued)

FOREIGN PATENT DOCUMENTS

| | | |
|---|---|---|
| EP | 2302353 A1 | 3/2011 |
| WO | WO 2009/126524 | 10/2009 |

OTHER PUBLICATIONS

Seok Chung et al., "Microfluidic Platforms for Studies of Angiogenesis, Cell Migration, and Cell-Cell Interactions," Annals of Biomedical Engineering, Biomedical Engineering Society, vol. 38, No. 3, Mar. 2010, pp. 1164-1177.

(Continued)

*Primary Examiner* — Gautam Prakash
(74) *Attorney, Agent, or Firm* — Hammer & Associates, P.C.

(57) ABSTRACT

Apparatuses, systems, and methods for generating concentration gradients of soluble molecules are disclosed herein.

(Continued)

Devices and methods for generating in vitro blood vessels are also disclosed.

5 Claims, 15 Drawing Sheets

(56) References Cited

U.S. PATENT DOCUMENTS

| | | |
|---|---|---|
| 2006/0154361 A1 | 7/2006 | Wikswo et al. |
| 2007/0178582 A1 | 8/2007 | Koser |
| 2008/0014575 A1 | 1/2008 | Nelson |
| 2008/0020368 A1 | 1/2008 | Yang et al. |
| 2008/0261306 A1 | 10/2008 | Neumann |
| 2011/0159522 A1 | 6/2011 | Kamm et al. |

OTHER PUBLICATIONS

Duffy et al., "Rapid prototyping of microfluidic systems in poly(dimethylsiloxane)," Anal.Chem. 1998, vol. 70, No. 23; pp. 4974-4984.

Carlos P. Huang et al., "Engineering microscale cellular niches for three-dimentional multicellular co-cultures," Lap Chip, (vol. 9), (p. 1740-1748), (2009).

Wei Tan et al., "Microscale multilayer cocultures for biomimetic blood vessels," Journal of Biomedical Materials Research Part A, Wiley Periodicals, Inc., (vol. 72A), (Issue 2), (p. 146-160), (Feb. 1, 2005).

DEVICE AND METHOD OF 3-DIMENSIONALLY GENERATING IN VITRO BLOOD VESSELS

CROSS-REFERENCE TO RELATED APPLICATION

This is a Divisional Application of co-pending U.S. application Ser. No. 13/089,130 filed Apr. 18, 2011 which claims priority to U.S. application Ser. No. 11/849,194 filed Aug. 31, 2007, a continuation-in-part application and now U.S. Pat. No. 7,947,491, which claims priority to U.S. Provisional Application Ser. No. 60/841,721 filed Aug. 31, 2006, and to U.S. Provisional Application Ser. No. 60/841,798 filed Aug. 31, 2006. The entire disclosures of application Ser. Nos. 11/849,194 and 13/089,180 are incorporated herein by reference in its entirety.

TECHNICAL FIELD

Provided herein are apparatuses, systems and methods for generating concentration gradients of soluble molecules. Also, provided herein are devices and methods for generating in vitro blood vessels.

BACKGROUND

In the chemical, biomedical, bioscience and pharmaceutical industries, it has become increasingly desirable to perform large numbers of chemical operations in a highly parallel fashion. The formation of microfluidic concentration gradients can facilitate such operations. Microfluidic devices and systems provide improved methods of performing chemical, biochemical and biological analysis and synthesis. Chip-based microfluidic systems have been developed. Typically, such devices include chambers and reservoirs connected by channels. Reproducible and cost-effective devices, systems and methods for forming temporal and spatial microfluidic concentration gradients in 2D and 3D environments are desirable.

SUMMARY

The present application relates, in general, to the field of devices and systems for generating and maintaining a chemical gradient. In particular, the present application relates to devices that make use of a gradient chamber or gradient bridge associated with source and sink channels to facilitate the generation of a stable gradient in an environment suitable for facilitating molecular events. In some embodiments, the devices systems and methods facilitate the identification of factors that modulate molecular events such as cell migration or the formation and isolation of crystallized molecules.

Accordingly, in one embodiment a gradient device is provided. The device includes a source channel in fluid communication with a first inlet; a sink channel in fluid communication with a second inlet and substantially parallel to the first channel; and at least one gradient chamber substantially proximal to the source channel and the sink channel. The terminal ends of the gradient are fluidly connected to the first channel and the second channel. In general, the dimensions of the gradient chamber are suitable for forming a gradient generating region substantially exclusively by diffusion.

In another embodiment, a gradient device is provided. The device includes a source channel in fluid communication with a first inlet and a sink channel in fluid communication with a second inlet and substantially parallel to the source channel. The device further includes at least one gradient bridge disposed in proximity to the source channel and sink channel, the gradient bridge optionally in fluid communication with a bridge channel and including at least a first aperture in fluid communication with the source channel and at least a second aperture in fluid communication with the sink channel. In general, the gradient bridge and the gradient channel are configured to i) facilitate the formation of a gradient generating region substantially exclusively by diffusion and ii) contain a matrix suitable for sustaining cell migration.

In another embodiment, a platform that includes a plurality of gradient devices is provided.

In yet another embodiment, a system is provided. The system includes a gradient device or platform as provided herein. The system further includes a controller operably associated with the gradient device or platform, or any combination thereof. In general, the controller is configured to control fluid movement through the channels during operation of the device or platform. The system also includes a detector assembly configured to capture a molecular event associated with a gradient generating region.

In yet another embodiment, a method of generating a gradient is provided. The method includes introducing a source constituent into the source channel of a device provided herein and introducing a sink constituent into the sink channel of a device provided herein. Further providing a constant flow of source constituent and sink constituent and generating a gradient in the gradient chamber or gradient bridge of a device provided herein. The gradient includes a substantially constant gradient profile.

The present application also relates, in general, to the field of devices and methods for generating perfusable, connected network of blood vessels with lumens in vitro in 3D gels.

In one embodiment of the present invention, the blood vessel-generating device includes a sink channel in fluid communication with a sink inlet; a source channel in fluid communication with a source inlet substantially parallel to the sink channel; and at least one blood vessel chamber disposed between the sink channel and the source channel and including at least a first terminal end in fluid communication with the sink channel and at least a second terminal end in fluid communication with the source channel. Here, the at least one blood vessel chamber is arranged to correspond to the thickness and length of the blood vessel to be generated, and arranged to form a blood vessel-generating region by filling a gel and/or an extracellular matrix (ECM).

Another exemplary embodiment of the present invention relates to a method of generating a blood vessel including filling a gel and/or an extracellular matrix (ECM) into the blood vessel chamber of the blood vessel-generating device; injecting a blood vessel-forming cell into the sink channel and/or the source channel of the blood vessel-generating device and attaching the blood vessel-forming cell to the gel and/or the ECM exposed to the first terminal end and second terminal end of the blood vessel chamber; and injecting an angiogenesis factor and a cell culture medium into the sink channel and/or the source channel of the blood vessel-generating device and culturing the blood vessel-forming cell.

In yet another exemplary embodiment of the present invention, the blood vessel-generating device includes a sink channel in fluid communication with a sink inlet; a source channel in fluid communication with a source inlet substantially parallel to the sink channel; a blood vessel-forming channel in fluid communication with a blood vessel-forming channel inlet, disposed in contact with the sides of the sink channel and the source channel between the sink channel and the source channel, substantially parallel to the source channel and the sink channel; a first culture channel in fluid communication with a first culture channel inlet, disposed in contact with the other side of the sink channel, substantially parallel to the sink channel; and a second culture channel in fluid communication with a second culture channel inlet, disposed in contact with the other side of the source channel, substantially parallel to the source channel. Here, a plurality of microstructures configured to allow interaction between biochemical materials included in each channel are arranged in the interfaces of the respective adjacent channels at set intervals.

Yet another exemplary embodiment of the present invention relates to a method of generating a blood vessel including injecting i) a gel and/or an ECM and ii) a blood vessel-forming cell into the blood vessel-forming channel of the blood vessel-generating device; injecting i) the gel and/or the ECM and ii) a co-culturing cell into the first culture channel and/or the second culture channel of the blood vessel-generating device; and injecting an angiogenesis factor and a cell culture medium into the sink channel and/or the source channel of the blood vessel-generating device and culturing the blood vessel-forming cell and the co-culturing cell.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIG. 3 panel B depicts an embodiment of a gradient device including exemplary gradient bridges suitable for generating gradients in three-dimensions;

FIG. 3 panel C depicts an exemplary gradient chamber including apertures suitable for producing a non-linear gradient;

FIG. 3 panel D depicts an exemplary gradient channel including asymmetric apertures suitable for producing a non-linear gradient;

FIG. 4 panel B depicts an exemplary gradient profile (right panel) and fluorescent images (left panel) produced by a gradient device provided herein;

FIG. 4 panel C depicts an exemplary gradient profile (right panel) and fluorescent images (left panel) produced by a gradient device provided herein;

FIG. 5 panel B depicts a phase micrograph of the gradient chambers shown in FIG. 5 panel A;

FIG. 5 panel C depicts a cross section of an embodiment of a gradient device;

FIG. 6 panel B depicts a phase micrograph of collagen gels formed in the gradient bridges shown in FIG. 6 panel A;

FIG. 6 panel C depicts a phase micrograph of collagen gels formed in the gradient bridges shown in FIG. 6 panel A;

DETAILED DESCRIPTION

Devices, systems and methods for the efficient generation of concentration gradients in two-dimensional (2D) and three dimensional (3D) environments are provided.

Figure 1:
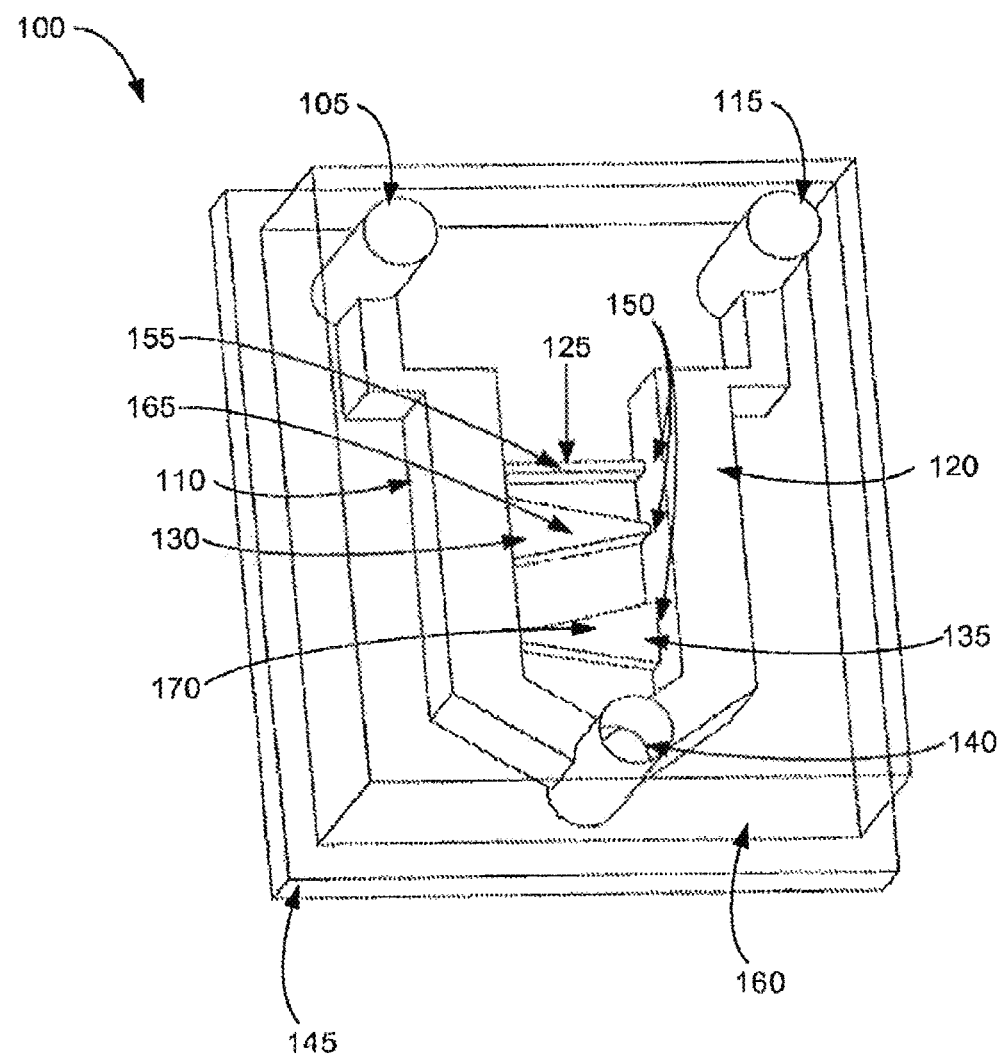
FIG. 1 depicts an embodiment of a gradient device including exemplary gradient chambers.

An exemplary embodiment of a gradient generating device is depicted in FIG. 1. Gradient device 100 includes base 145 associated with substrate 160. Substrate 160 includes sink inlet 105 which provides for the movement of materials (either by mass fluid flow or molecular diffusion) into sink channel 110, and outlet 140 which provides for movement of materials out of sink channel 110 and source channel 120. Sink channel 110 and source channel 120 may be associated with sink inlet 105 and source inlet 115, respectively. It is understood that while FIG. 1 depicts a common outlet for sink channel 110 and source channel 120, devices provided herein encompass the use of individual outlet channels associated with each channel. Source inlet 115 provides for the movement of a source constituent (either by mass fluid flow or molecular diffusion) into source channel 120. Sink inlet 105 provides for the movement of a sink constituent (either by mass fluid flow or molecular diffusion) into sink channel 110. At least one gradient chamber is located in proximity to, and in fluid communication with, sink channel 110 and source channel 120. FIG. 1 depicts multiple exemplary gradient chambers suitable for forming gradients. Symmetric gradient chamber 125 is suitable for generating a linear gradient in gradient generating region 155. Asymmetric gradient chamber 130 is suitable for generating a non-linear gradient in gradient generating region 165. Asymmetric gradient chamber 135 is suitable for generating a non-linear gradient in gradient generating region 170. Substrate 160 includes channels, chambers, inlets, outlets and other elements associated with gradient device 100 or 200 (see FIG. 2). Substrate 160 can be manufactured from any material suitable for forming microfluidic structures associated with the transport of minute quantities of substances.

The formation of a gradient in a gradient generating region 155, 165, 170 may be modulated by various modifications to the device. For example, the height of the gradient chamber 150 in relation to the source and sink channel can be modified. As the device generates gradients across a gradient generating region by free-diffusion between a source and a sink channel, convective flow through a gradient chamber may be minimized by designing the height of the gradient chamber to be substantially less than that of the main channels (e.g. the source and sink channels. The gradient chamber height to sink or source height ratio can be 1:2, 1:5, 1:10, 1:15, 1:20, 1:25, 1:30, 1:40, 1:50, 1:75, 1:100 or 1:500. In practice, a large difference in gradient chamber height yields an even larger difference in fluidic resistance causing flow to take the path of least resistance (e.g., sink or source channel) rather than entering the gradient chamber, allowing only diffusive transport.

A source constituent and sink constituent are included in source channel and sink channel, respectively. Diffusion occurs between a source constituent and a sink constituent which are in fluid communication with each other via a gradient chamber (see FIG. 1) or gradient bridge (see FIG. 2). Free-diffusion between source and sink constituents occurs through the finite volume of a gradient chamber or gradient bridge, producing a concentration gradient which can be detected and/or measured.

Based upon the biologic or chemical structure of the sink constituent, the presence or absence of the source constituent's diffusion rate toward the sink constituent, and/or the rate of that diffusion, the activity of the source constitute can be ascertained. Analogously, knowledge of the biologic or chemical makeup of the source constituent and the aforementioned presence (or absence) and source constituent's rate of diffusion, conclusions as to the activity of the sink constituent can be made. For generating crystalline structures of a target molecule, the target molecule can be included in the sink constituent in the presence of a particular buffer. The source constituent may contain a similar buffer but at a different pH and/or including a different salt concentration. The gradient will form in a gradient generating region reflecting the diffusion of the source and sink constituents, thereby facilitating formation of a crystal structure of the target molecule in the region. In this example, the detectable molecular event includes the formation of a crystalline structure of a target molecule.

Figure 3:
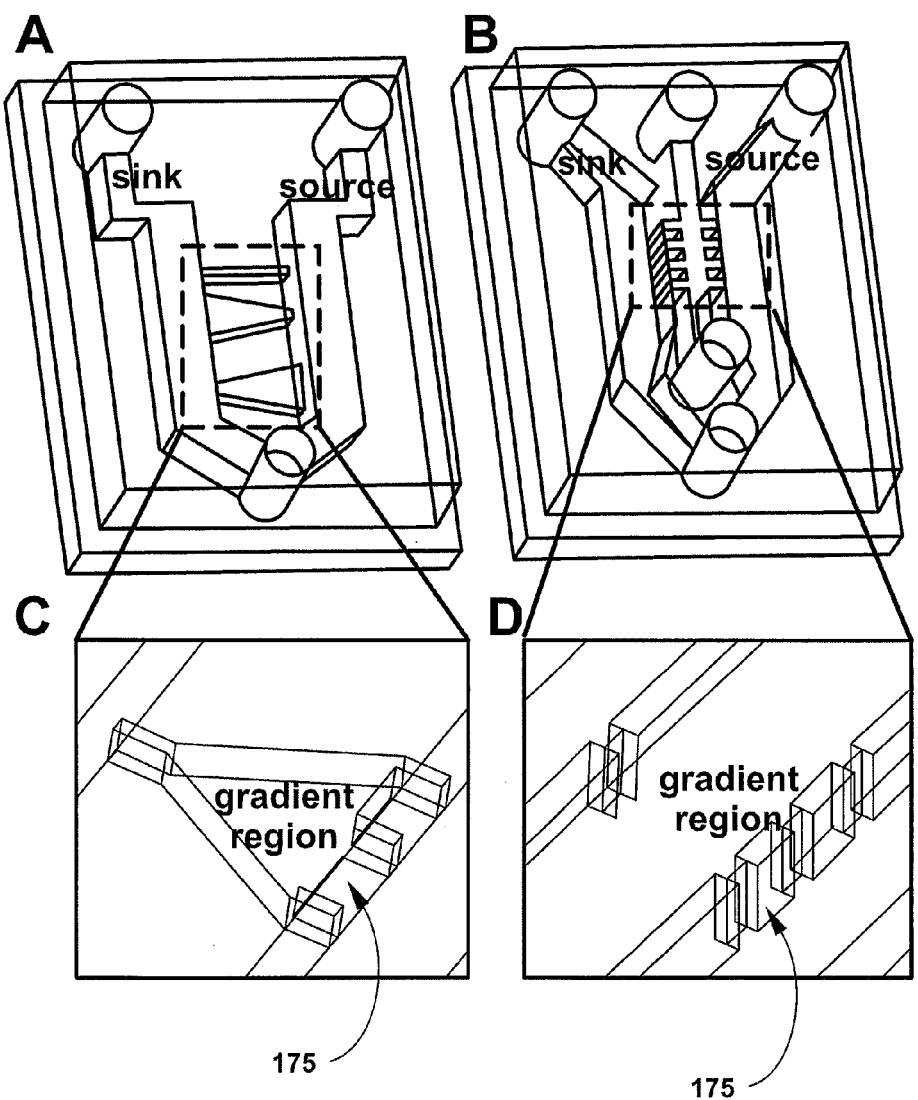
FIG. 3 panel A depicts an embodiment of a gradient device including exemplary gradient chambers suitable for generating gradients in two-dimensions.

Referring to FIG. 3 panel C, additional modifications include post structure 175 situated at or near the interface of a gradient chamber and main channels. Such structures may provide additional resistance when large opening are needed for non-linear gradient profiles.

Linear gradients may be generated when the interface conditions are such that the molecular flux area is constant across a gradient generating region, as in a straight channel (see e.g., FIG. 1, element 125). The generation of non-linear profiles useful for both chemical and biological conditions may be achieved by modifying the flux area associated with the gradient generating region. Referring to FIG. 1, modifying the geometric design of the gradient chamber and the relative openings to source and sink channels may be used to modulate a gradient profile. A symmetric gradient chamber (see e.g., element 125) may produce a linear gradient profile where the slope of the gradient is substantially dependent on the length of the gradient generating region.

Non-linear profiles may be produced by manufacturing a gradient chamber in an asymmetric configuration (see e.g., elements 130 and 135). This arrangement provides a continual imbalance of the in-flux and out-flux area between the source and sink channels through which molecules diffuse. The degree of non-linearity may also be changed by curved gradient chambers.

Gradient profiles may also be controlled by modifying the ratio of the number of sink to source openings (e.g., the area of the gradient generating region through which molecules diffuse). Linear gradients may be produced when the openings are symmetric and evenly distributed at opposite ends since the in-flux and out-flux area of the diffusing molecules are equal. Non-linear gradients may be produced when the number of openings are unbalanced causing an unequal in-flux and out-flux area in the gradient generating region. The degree of non-linearity can be enhanced by increasing the ratio of openings and shortening the width of the gradient generating region.

Further, gradient profiles may be controlled by modifying the concentrations of the source and sink constituents, which can be further controlled temporally by switching the inlet solutions.

Also encompassed by embodiments of gradient devices provided herein are complex gradient profiles made by a serial combination of a plurality of gradient chamber or gradient bridge designs within a gradient generating region. For example, juxtaposing a concave down and concave up non-linear profile will yield a sigmoidal gradient profile. For the gradient device shown in FIG. 1, this may be achieved by arranging the gradient chamber in a "bow-tie" shape with wide openings to the source and sink channels and tapering towards the middle of the chamber. For the gradient device shown in FIG. 2, a complex gradient profile may be achieved by configuring multiple gradient generating regions to include multiple apertures to the source and sink channels on the outer sides and fewer connecting apertures in the middle. Additionally, since various types of gradient device designs can be integrated during fabrication, a variety of both linear and non-linear profiles can be generated on a single device or platform for high-throughput experiments.

Figure 2:
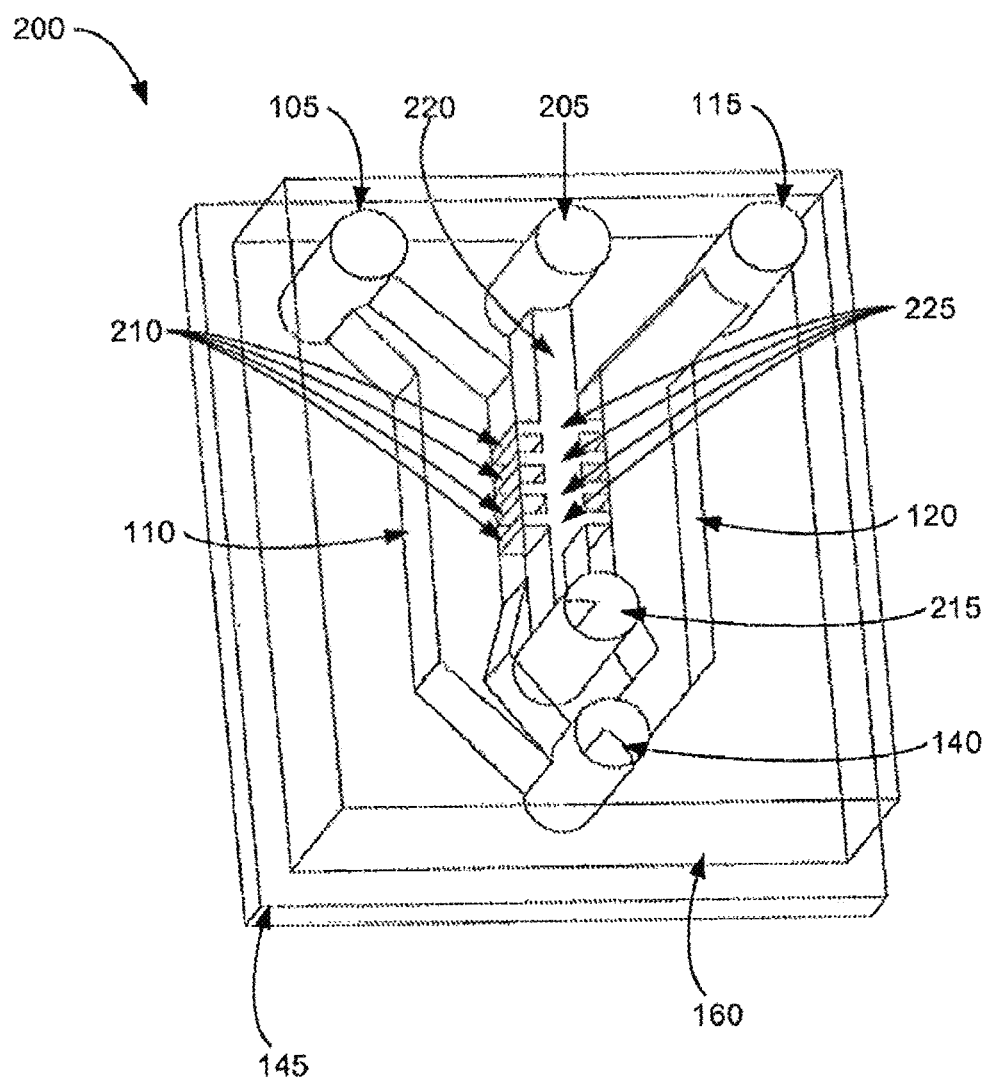
FIG. 2 depicts an embodiment of a gradient device including an exemplary bridge channel including a plurality of gradient bridges.

A second exemplary embodiment of a gradient generating device is depicted in FIG. 2. Gradient device 200 is configured to include gradient bridge 210 fluidly associated with sink channel 110 and source channel 120. It is understood that while FIG. 2 depicts multiple gradient bridges, a gradient device that includes a single gradient bridge is also encompassed by this embodiment. Gradient bridge 210 is configured to facilitate the formation of gradient generating region(s) 225. Gradient device optionally includes bridge channel 220 fluidly associated with gradient bridge 210. Bridge channel is a fluidly associated with bridge channel inlet 205.

Gradient generating device 200 may be configured to accommodate a matrix functionally associated with gradient bridge 210 and optionally bridge channel 220. In this embodiment, the formation of a gradient in a gradient generating region 225 occurs within the matrix. As the device generates gradients across a gradient generating region by free-diffusion between a source and a sink channel, convective flow through a gradient chamber may be minimized by selectively filling the gradient generating region with a 3D matrix (e.g., collagen gel) which increases the fluidic resistance minimizing flow penetration into the gradient generating region. Referring to FIG. 3 panel D, additional modifications include post structure 175 situated at or near the interface of a gradient bridge and main channels. Such structures may provide additional resistance when large opening are needed for non-linear gradient profiles.

Gradient generating device 200 including a matrix provides conditions suitable for studying cell motility and chemotaxis in the presence of a gradient containing a soluble factor. For example, a soluble factor may be present in the source constituent. The source constituent may be added to source channel 115. A cell may be added to the matrix associated with gradient bridge 210 or bridge channel 220. Sink channel 110 containing sink constituent (i.e. source constituent minus soluble factor). A gradient of soluble factor forms in bridge channel a gradient generating region 225. Cell activity in relation to the gradient can be determined by e.g., microscopy.

The generation of linear and non-linear gradients may be accomplished. Referring to FIG. 3 panels B and D, modifying the geometric design of the gradient bridge and the relative openings to source and sink channels may be used to modulate a gradient profile in a matrix. Gradient profiles may be controlled by modifying the ratio of the number of sink to source openings (e.g., the area of the gradient generating region through which molecules diffuse). Linear gradients may be produced when the openings are symmetric and evenly distributed at opposite ends since the in-flux and out-flux area of the diffusing molecules are equal. Non-linear gradients may be produced when the number of openings are unbalanced causing an unequal in-flux and out-flux area in the gradient generating region. The degree of non-linearity can be enhanced by increasing the ratio of openings and shortening the width of the gradient generating region.

Also encompassed by embodiments of gradient devices provided herein are complex gradient profiles made by a serial combination of a plurality of gradient chamber or gradient bridge designs within a gradient generating region. For the gradient device shown in FIG. 2, a complex gradient profile may be achieved by configuring multiple gradient generating regions to include multiple apertures to the source and sink channels on the outer sides and fewer connecting apertures in the middle. Additionally, since various types of gradient device designs can be integrated during fabrication, a variety of both linear and non-linear profiles can be generated on a single device or platform for high-throughput experiments. The following published applications are incorporated herein by reference in their entirety: U.S. Publication No. 20040106192, U.S. Publication No. 20040121066, and U.S. Publication No. 20050217750. The term "microfluidic" refers to a system or device for handling, processing, ejecting and/or analyzing a fluid sample including at least one channel having microscale dimensions. The terms "channel," "sink channel," or "source channel" as used herein refers to a pathway formed in or through a medium that allows for movement of fluids, such as liquids and gases. The channel in a device or system provided herein may include cross-sectional dimensions in the range between about 1.0 .mu.m and about 500 .mu.m, between about 25 .mu.m and about 250 .mu.m and between about 50 .mu.m and about 150 .mu.m. One of ordinary skill in the art will be able to determine an appropriate volume and length of the channels. The ranges are intended to include the above-recited values as upper or lower limits. A channel can have any selected shape or arrangement, examples of which include a linear or non-linear configuration and a U-shaped configuration.

Microfluidic gradients created in accordance with the devices and methods as described herein may be useful in a variety of applications. As specifically described in detail below, the flow-free diffusion that occurs at the gradient generating region (GGR) may provide conditions advantageous in the formation of crystals, as well as in the performance of certain assays for cell motility and chemotaxis.

Figure 4:
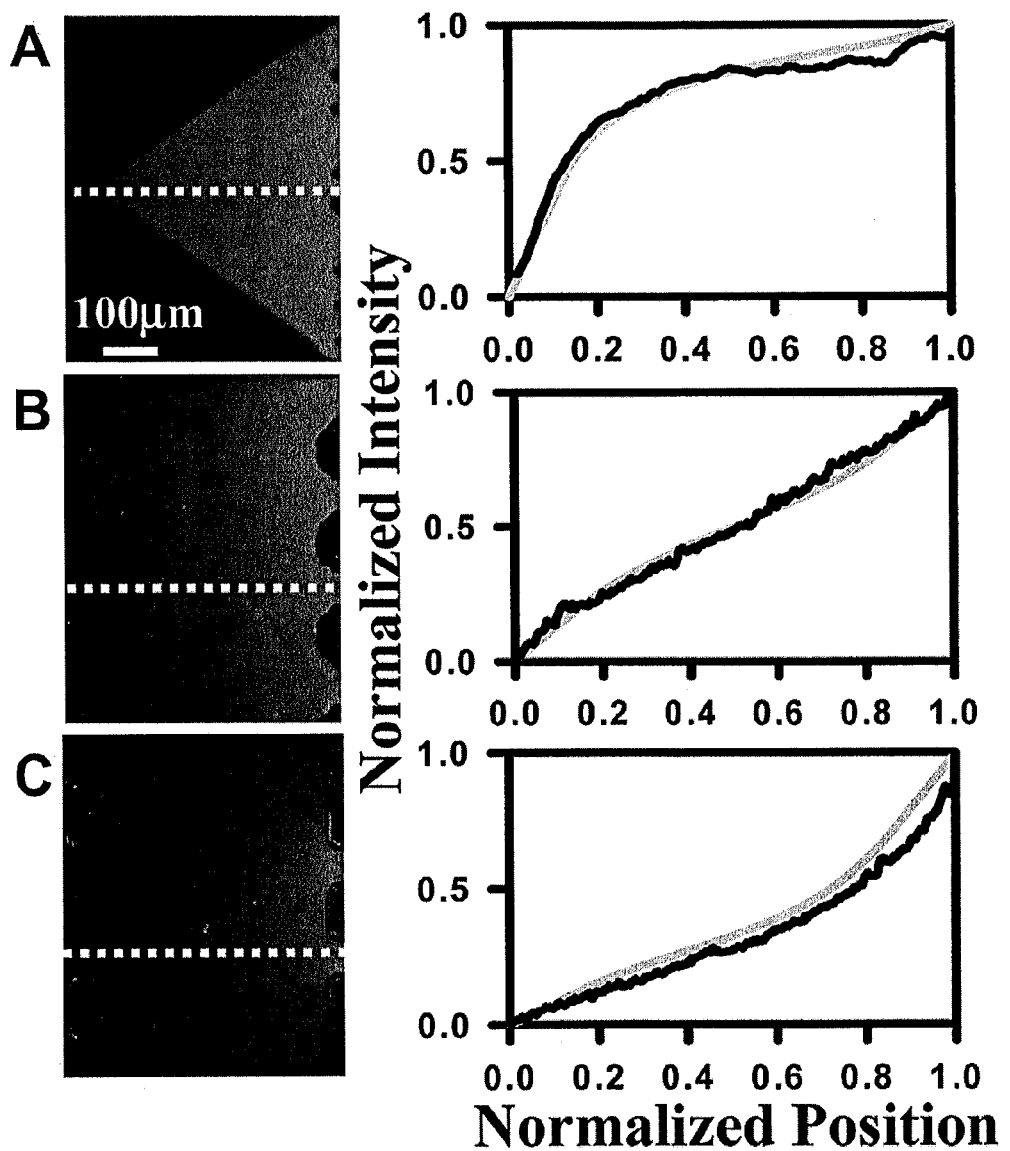
FIG. 4 panel A depicts an exemplary gradient profile (right panel) and fluorescent images (left panel) produced by a gradient device provided herein.
Figure 5:
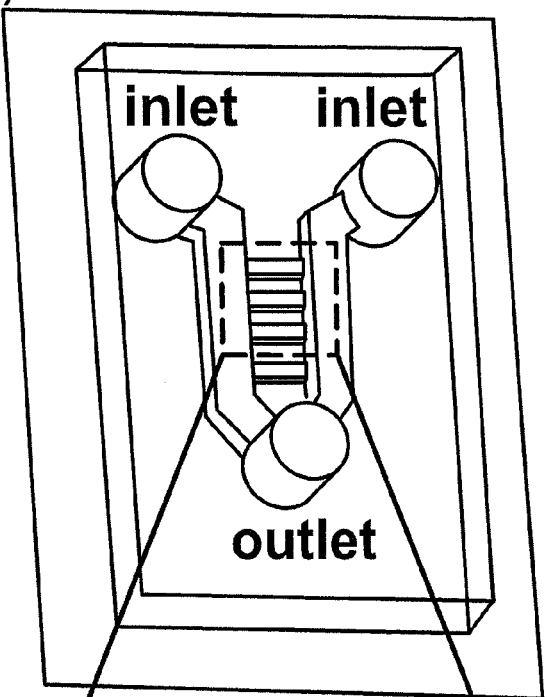
FIG. 5 panel A depicts an embodiment of a gradient device including a plurality of gradient chambers.
Figure 5:
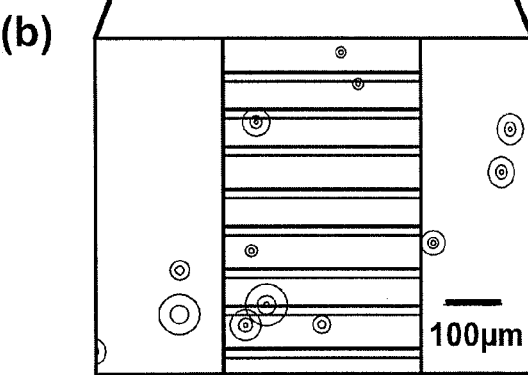
Figure 5:
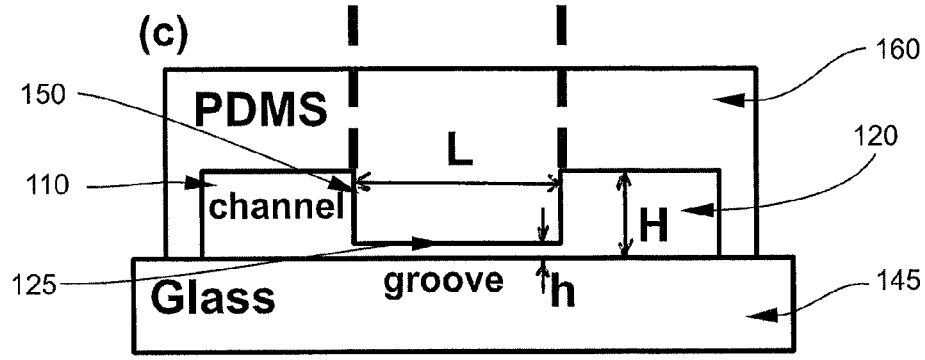
Figure 6:
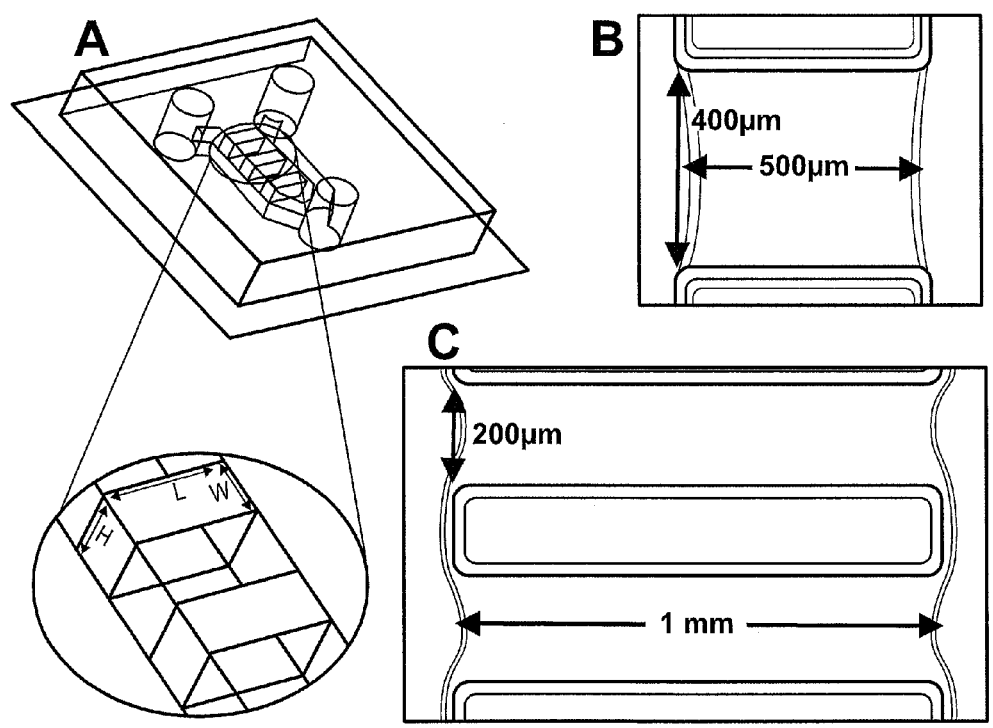
FIG. 6 panel A depicts an embodiment of a gradient device including a plurality of gradient bridges.

Provided herein are devices and methods suitable for facilitating free-diffusion between dynamically replenished flow channels acting as a sink and source to give rise to stable steady-state profiles. Such devices are particularly well-suited for forming 3D matrices for studying a molecular event associated with cell migration and/or the activity of a cell in a particular microenvironment. Referring again to FIG. 3 panel B, the gradient generating region in this embodiment includes a 3D matrix. FIG. 3 panel D depicts a gradient generating region for a 3D matrix with asymmetric posts designed to produce non-linear gradient. FIG. 4 depicts fluorescent images and corresponding experimental (black) and theoretical (grey) gradient profiles across GGR; intensity profiles taken across white dash line. FIG. 4 panel B depicts gradients across 3D matrigel produced using a design shown in FIG. 2 or FIG. 3, panel B. Linear profiles were produced by designing the same number of openings to source and sink channels. Referring to FIG. 4 panel C, mismatched number of openings to source and sink channels resulted in a non-linear profile. The openings were about 50.mu.m wide.

Devices and methods provided herein are suitable for studying live cells. For example, the devices can be used to successfully observe chemotaxis of a cell in a gradient of a soluble factor such as, for example, a chemokine. The device can be placed on a microscope during the experiment and time-lapse micrographs taken at various intervals. Computer controlled pumps can used to infuse agents such as media or chemokines into the device. For example, human cancer cells chemotax when exposed to gradients of a variety of growth factors. A gradient device provided herein can be used to examine the behavior of cells in a controlled fluidic microenvironment containing autocrine/paracrine factors for cell signaling investigations.

Referring again to FIG. 1, a gradient device provided herein can be used to produce crystalline structures of target molecules. Crystallization is an important technique to the biological and chemical arts. A high-quality crystal of a target molecule can be analyzed by x-ray diffraction techniques to produce an accurate three-dimensional structure of the target. This three-dimensional structure information can then be utilized to predict functionality and behavior of the target. Forming a high quality crystal is generally difficult. The gradient devices and methods provided herein are particularly suited to crystallizing biological macromolecules or complexes thereof, such as proteins, nucleic acids, viruses, and protein/ligand assemblies. However, devices and methods provided herein are not limited to any particular type of target material.

In general, protein crystallization may be accomplished utilizing a device provided herein. For example, referring to FIG. 1, a gradient can be formed by introducing a source constituent into a source channel, and introducing a sink constituent containing a countersolvent or crystallizing agent into sink channel. A gradient is formed at the gradient generating region in the gradient chamber, thereby allowing for formation of a diffusion gradient between the source constituent and the sink constituent containing the crystallizing agent. As a result of diffusive mixing between the sample and the crystallizing agent, the solution environment is gradually changed, resulting in the formation of protein crystals in the chamber.

Typical targets for crystallization are diverse. A target for crystallization may include but is not limited to: 1) biological macromolecules (cytosolic proteins, extracellular proteins, membrane proteins, DNA, RNA, and complex combinations thereof), 2) pre- and post-translationally modified biological molecules (including but not limited to, phosphorylated, sulfolated, glycosylated, ubiquitinated, etc. proteins, as well as halogenated, abasic, alkylated, etc. nucleic acids); 3) deliberately derivatized macromolecules, such as heavy-atom labeled DNAs, RNAs, and proteins (and complexes thereof), seleno methionine-labeled proteins and nucleic acids (and complexes thereof), halogenated DNAs, RNAs, and proteins (and complexes thereof), 4) whole viruses or large cellular particles (such as the ribosome, replisome, spliceosome, tubulin filaments, actin filaments, chromosomes, etc.), 5) small-molecule compounds such as drugs, lead compounds, ligands, salts, and organic or metallo-organic compounds, and 6) small-molecule/biological macromolecule complexes (e.g., drug/protein complexes, enzyme/substrate complexes, enzyme/product complexes, enzyme/regulator complexes, enzyme/inhibitor complexes, and combinations thereof). Such targets are the focus of study for a wide range of scientific disciplines encompassing biology, biochemistry, material sciences, pharmaceutics, chemistry, and physics.

During crystallization screening, a large number of chemical compounds may be employed. These compounds include salts, small and large molecular weight organic compounds, buffers, ligands, small-molecule agents, detergents, peptides, crosslinking agents, and derivatizing agents. Together, these chemicals can be used to vary the ionic strength, pH, solute concentration, and target concentration in the drop, and can even be used to modify the target. The desired concentration of these chemicals to achieve crystallization is variable, and can range from nanomolar to molar concentrations. A typical crystallization mix contains set of fixed, but empirically-determined, types and concentrations of 'precipitants', buffers, salts, and other chemical additives (e.g., metal ions, salts, small molecular chemical additives, cryo protectants, etc.). Water is a key solvent in many crystallization trials of biological targets, as many of these molecules may require hydration to stay active and folded.

Precipitating agents act to push targets from a soluble to insoluble state, and may work by volume exclusion, changing the dielectric constant of the solvent, charge shielding, and molecular crowding. Precipitating agents compatible with the PDMS material of certain embodiments of the device provided herein include, but are not limited to, salts, high molecular weight polymers, polar solvents, aqueous solutions, high molecular weight alcohols, and divalent metals.

Precipitating compounds, which include large and small molecular weight organics, as well as certain salts, are used from under 1% to upwards of 40% concentration, or from less than 0.5 M to greater than 4 M concentration. Water itself can act in a precipitating manner for samples that require a certain level of ionic strength to stay soluble. Many precipitants may also be mixed with one another to increase the chemical diversity of the crystallization screen. The gradient devices described herein are readily compatible with a broad range of such compounds. Moreover, many precipitating agents (such as long- and short-chain organics) are quite viscous at high concentrations, presenting a problem for most fluid handling devices, such as pipettes or robotic systems.

Solution pH can be varied by the inclusion of buffering agents; typical pH ranges for biological materials lie anywhere between values of 3.5-10.5 and the concentration of buffer, generally lies between 0.01 and 0.25 M. The gradient devices described in this document are readily compatible with a broad range of pH values, particularly those suited to biological targets.

A nonexclusive list of possible buffers is as follows: Na/K-Acetate; HEPES; Na-Cacodylate; Na/K-Citrate; Na/K-Succinate; Na/K-Phosphate; TRIS; TRIS-Maleate; Imidazole-Maleate; BisTrisPropane; CAPSO, CHAPS, MES, and imidizole.

Additives are small molecules that affect the solubility and/or activity behavior of the target molecule. Such compounds can speed crystallization screening or produce alternate crystal forms of the target. Additives can take nearly any conceivable form of chemical, but are typically mono and polyvalent salts (inorganic or organic), enzyme ligands (substrates, products, allosteric effectors), chemical cross-linking agents, detergents and/or lipids, heavy metals, organo-metallic compounds, trace amounts of precipitating agents, and small and large molecular weight organics.

In addition to chemical variability, a host of other parameters can be varied during crystallization screening. Such parameters include but are not limited to: 1) volume of crystallization trial, 2) ratio of target solution to crystallization solution, 3) target concentration, 4) cocrystallization of the target with a secondary small or macromolecule, 5) hydration, 6) incubation time, 7) temperature, 8) pressure, 9) contact surfaces, 10) modifications to target molecules, and 11) gravity.

Volumes of crystallization trials can be of any conceivable value, from the picoliter to milliliter range. Typical values may include but are not limited to: 0.1, 0.2, 0.25, 0.4, 0.5, 0.75, 1, 2, 4, 5, 10, 15, 20, 25, 30, 35, 40, 45, 50, 60, 70, 75, 80, 90, 100, 125, 150, 175, 200, 225, 250, 275, 300, 350, 400, 450, 500, 550, 600, 700, 750, 800, 900, 1000, 1100, 1200, 1250, 1300, 1400, 1500, 1600, 1700, 1800, 1900, 2000, 2250, 2500, 3000, 4000, 5000, 6000, 7000, 7500, 8000, 9000, and 10000 mL. The gradient devices previously described can access these values.

In particular, access to the low volume range for crystallization trials (<100 mL) is a distinct advantage of embodiments of the gradient devices provided herein. Small-volume gradient chambers for crystallization studies can be readily designed and fabricated, minimizing the need the need for large quantities of precious target molecules. The low consumption of target is particularly useful in attempting to crystallize scarce biological samples such as membrane proteins, protein/protein and protein/nucleic acid complexes, and small-molecule drug screening of lead libraries for binding to targets of interest.

Co-crystallization generally describes the crystallization of a target with a secondary factor that is a natural or normatural binding partner. Such secondary factors can be small, on the order of about 10-1000 Da, or may be large macromolecules. Co-crystallization molecules can include but are not limited to small-molecule enzyme ligands (substrates, products, allosteric effectors, etc.), small-molecule drug leads, single-stranded or double-stranded DNAs or RNAs, complement proteins (such as a partner or target protein or subunit), monoclonal antibodies, and fusion-proteins (e.g., maltose binding proteins, glutathione S-transferase, protein-G, or other tags that can aid expression, solubility, and target behavior). As many of these compounds are either biological or of a reasonable molecular weight, co-crystallization molecules can be routinely included with screens in the gradient generating devices.

Gradient device designs may include nonreactive, biocompatible environments. Thus, the composition of the gradient chambers in the gradient device can be varied to provide new surfaces for forming e.g., crystallized molecules. In addition, the small size of the gradient chambers allows e.g., crystallization attempts under hundreds or even thousands of different sets of conditions to be performed simultaneously.

Exemplary Materials and Methods

Provided herein are monolithic microfluidics-based gradient generating devices that can generate an array of complex steady-state soluble molecular gradients in flow-free 2D and 3D environments. Three dimensional hydrogels are increasingly used in the investigation of many cell behaviors as they simulate in-vivo conditions better than 2D models. Investigations on invasive migration of metastatic cancer cells and stem cell niches can benefit greatly if complex, stable molecular gradients can be achieved across 3D gels in flow-free conditions. The design principles provided herein may be applied to build complex profiles by simply engineering the shape of the gradient generating region as set forth in various embodiments of devices described herein. Continuously replenished source and sink are advantageous over static reservoirs because their concentration can be kept constant and thus the gradients can be maintained at constant profile at steady-state.

Device Fabrication: A master was made by two rounds of photolithography on a silicone wafer. The first layer patterns the gradient chambers or gradient bridges and the second layer patterns the source or sink channels. The transparency masks were drawn in Freehand 9.0, and then printed by PAGE ONE DIGITAL (Irvine, Calif.). The silicone wafer (Silicon, Inc.—Boise, Id.) was plasma cleaned (Harrick Scientific Corp.—Ossining, N.Y.) for a suitable time period (e.g., 5 minutes) and then covered with SU-8 5 photoresist (Microchem, Inc.—Newton, Mass.) by spincasting at about 3,500 rpm for about 1 min to yield a thickness of 3.3 .mu.m. The coated wafer was baked for 1 min at 100.degree. C. in a leveled oven. The wafer was then exposed to UV light for 7 seconds at 25 mW/cm.sup.2 and baked again for 1 min at 100.degree. C. Finally, the wafer was placed into developer removing SU-8 from unexposed regions. The patterned wafer was then air-dried and a second layer was applied using SU-8 50; the thickness is a 100 .mu.m by spincasting at 1,000 rpm for 1 minute. For aligning purposes, tape was used over the aligner marks so that the photoresist will not conceal them. The remaining features were then patterned with the same procedure as above except for baking and exposure time. After second layer coating, the wafer is baked for 30 min at 100.degree. C. and exposed to UV for 20 seconds at 25 mW/cm.sup.2. The wafer was baked again for 10 min at 100.degree. C. and then developed. The finalized wafer was then silanized in a desiccator for 2 hours and then placed in a plastic petri dish and filled with PDMS. PDMS was made using a 10:1 ratio of prepolymer and catalyst. The PDMS was baked at 80 .degree. C. for 3 hours to become fully polymerized. The PDMS pattern is then cut from the master mold with inlet and outlet holes punched out. A glass slide and the prepared device were plasma cleaned for 2 minutes. The device and slide glass were then sealed irreversibly together with channels formed at the interface.

Additional methods for manufacture a device provided herein are known to the skilled artisan. For example, in soft lithographic bonding, elastomeric layers may be bonded together chemically, using chemistry that is intrinsic to the polymers comprising patterned elastomer layers. The bonding may include two component "addition cure" bonding. The various layers of elastomer may be bound together in a heterogeneous bonding in which the layers have a different chemistry. Alternatively, a homogenous bonding may be used in which all layers would be of the same chemistry. Thirdly, the respective elastomer layers may optionally be glued together by an adhesive. In a fourth aspect, the elastomeric layers may be thermoset elastomers bonded together by heating.

The elastomeric layers may be composed of the same elastomer material, with the same chemical entity in one layer reacting with the same chemical entity in the other layer to bond the layers together. Alternatively, bonding between polymer chains of like elastomer layers may result from activation of a crosslinking agent due to light, heat, or chemical reaction with a separate chemical species.

Further, the elastomeric layers may be composed of different elastomeric materials, with a first chemical entity in one layer reacting with a second chemical entity in another layer. Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", Analytical Chemistry (1998), 70, 4974-4984, incorporated herein by reference. This paper discloses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Two different methods (depending on the device design) were used to selectively localize the gels in the gradient generating region. For devices with gradient bridge design (e.g., FIG. 2), the entire device was first filled with liquid gel followed by rapid aspiration with house vacuum. Since the resistance across the gradient generating region is considerably higher than across the main channels, the gel in the G gradient generating region were selectively left behind. The second method requires simple loading of liquid gel into the gradient generating region inlet and can be used with the design shown in FIG. 3 panel B. After plasma treatment and bonding, channel surfaces were allowed to revert back to a hydrophobic state before injecting the gel into gradient generating region. The gel was confined to the gradient generating region by surface tension until it solidified and then used for gradient experiments. A number of gel materials such as collagen type I, Matrigel, and fibrin were successfully polymerized in the device using both methods.

Gradient Characterization: The gradient profiles were generated and compared through an experimental fluorescent image of a chemical gradient and a simulated model. The experimental gradient was formed by a fluorescent molecule Fluorescein isothiocyanate (FITC), isomer I, 90% (Aldrich—Steinheim, Germany) which has a molecular weight of 389.39 g/mole. The solutions used were deionized water and 1% FITC solution in deionized water. After the flow began by pumping (Harvard Apparatus Picoplus—Woodstock, Conn.) at 2.mu.l/min from each outlet, the device was allowed to reach steady-state and bright-field and fluorescent pictures were taken. Centerline intensity profiles were taken and normalized. These profiles were compared to simulated centerline concentration profiles that were also normalized. The simulated profiles were generated by a finite element modeling software designated Comsol 3.2. The simulated gradient profile is based on a system with the exact geometry of the transparency mask with solely diffusion as a means of transport from one end to the other. Diffusion as the sole means of transport was confirmed by flowing fluorescent bead through the main channels and observing that no beads convectively entered the gradient chamber or gradient bridge. The concentrations used were 100% and 0% signifying the use of a buffer on one side. For both the experimental and simulation, only the steady-state gradient profiles were evaluated. To ensure that steady-state was reached in the experiment, extra time was given to establish the gradient than predicted by the equation:

$$t = \frac{x^2}{2D}$$

where t is the time for the molecule to diffuse a distance, x is the distance the molecule will diffuse, and D is the diffusion coefficient.

In one exemplary device, the distance to be diffused may be 400 .mu.m and the diffusion coefficient may be that of the exemplary fluorescent molecule FITC which has a molecular weight of 389.39 g/mole. In order to calculate the diffusion coefficient, two equations may be implemented which approximate the linear size of the molecule and equates the diffusion coefficient. The first equation approximates the linear size:

$$a \approx MW^{\frac{1}{3}}$$

where, a is the linear molecule size, and MW is the molecular weight of a molecule.

The molecular weight of FITC is 389.39 g/mole. Accordingly, a single molecule is that divided by Avogadro's number, 6.022.times.10.sup.23 molecules/mole, which yields 6.466.times.10.sup.-22 g/molecule. Therefore a is equal to 8.65.times. 10.sup.-8 cm. The equation for the diffusion coefficient is:

$$D = \frac{kT}{6\pi\eta a}$$

where, k is the Boltzmann constant, T is the temperature, n is the fluid viscosity, and a is the linear molecule size. The values for T, 17, and a, are 300.degree. K, 0.01 g/cm/s, 8.65.times.10.sup.-8 cm, respectively; this calculates a value for D of 2.54.times.10.sup.-6 cm.sup.2/s. Utilizing this value for D approximates the steady-state time to be about 5.24 minutes.

The experimental data for intensity values may include data processing due to shadowing effects from the fluorescence signal in the main channels. In some embodiments, the main channels (e.g., source, sink and/or bridge channels) may be about 2 to 100 times the height of the side channels (e.g., gradient chamber or gradient bridge) which may result in a shadowing effect. This effect may be compensated for by subtracting an intensity linescan at a location where there is no side channel (e.g., gradient chamber or gradient bridge) from the linescan taken at the desired side channel. Accordingly, the first part of the data processing may follow the equation $$I_f = I_{sc} - I_{ref}$$

where I.sub.f is the plotted intensity value, I.sub.sc is the intensity value taken at the side channel, and I.sub.ref is the intensity value taken at a reference location. This removes both the ambient signal from the main channels and background noise from the signal originating in the side channel.

The second part of the data processing may include normalizing both the intensity values and the positions along the channel so that the experimental and theoretical graphs align. The normalization subtracts the minimum intensity value within the line profile from each intensity value and then divides each value by the difference between the maximum and minimum intensity values. The normalization equation is written as:

$$\sum_{x=0}^{L} I(x)_{norm} = \frac{I(x) - I_{min}}{I_{max} - I_{min}}$$

where I(x).sub.norm is the normalized intensity value for a given pixel, I(x) is the intensity value calculated from the above equation for a given pixel, I.sub.min is the minimum intensity value of the linescan, I.sub.max is the maximum intensity value of the linescan, and L is the number of pixels in the linescan.

Figure 7:
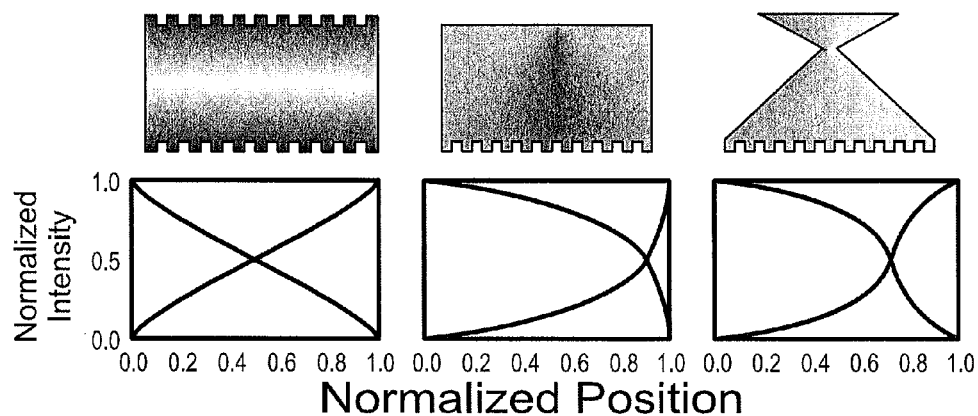
FIG. 7 depicts gradient profiles of three exemplary gradient chambers.

Referring to FIG. 7, profiles of three exemplary gradient chambers with their corresponding centerline gradient profile from both directions are provided. The left chamber yields a linear gradient, the middle chamber yields a non-linear gradient, and the right chamber is a juxtaposition of a concave-down and concave up non-linear gradient yielding an overall sigmoidal gradient profile.

Figure 8:
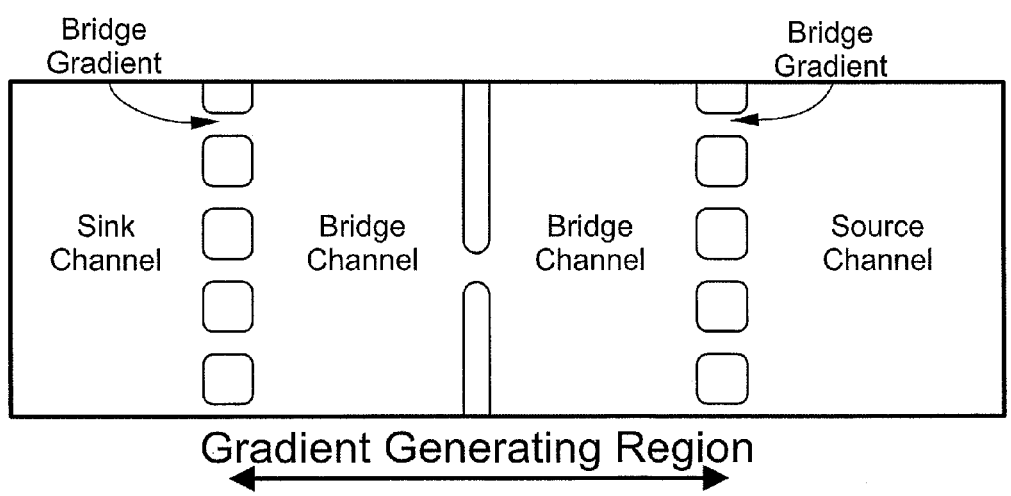
FIG. 8 depicts a collagen gel micrograph of an embodiment of a gradient device.

Collagen Gel Micrograph: Referring to FIG. 8, a micrograph of a collagen gel selectively polymerized in the gradient generating region of a gradient device is provided. In this embodiment, two juxtaposed bridge channels are shown in the gradient generating region. Gradient bridges appear as apertures between the "squares" flanking the bridge channels. In this embodiment, the gradient bridges provide fluid access from the source and sink channels to the bridge channel(s).

Figure 9:
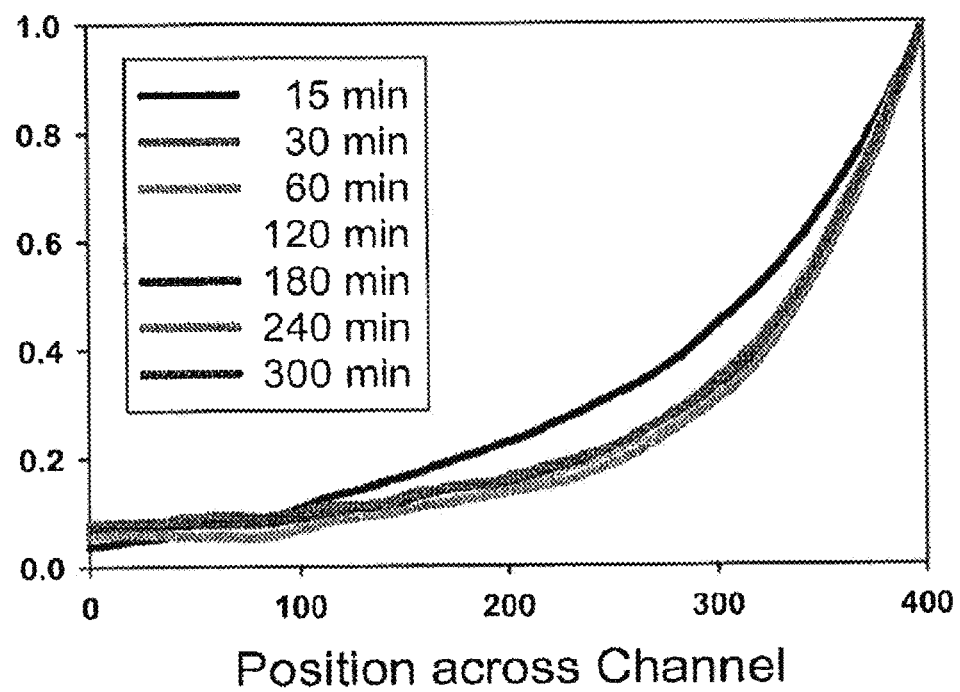
FIG. 9 depicts a graph of an exemplary concentration profile of a non-linear gradient across a collagen type 1 gel.

Gradient Stability over Time: A gradient device provided herein is suitable for maintaining a stable gradient over time. Such stability may depend upon the continual flow of source constituent and/or sink constituent through the main channels (e.g., the source, sink and/or bridge channels) of the device. Therefore after the steady-state gradient profile is reached, the profile will remain constant in the absence of flow disruption. FIG. 9 provides a graph of an exemplary concentration profile, taken over several time points, of a non-linear gradient across a collagen type 1 gel.

In addition, devices and methods of 3-dimensionally generating in vitro blood vessels are provided.

The blood vessel-generating device according to the present invention includes a sink channel in fluid communication with a sink inlet; a source channel in fluid communication with a source inlet substantially parallel to the sink channel; and at least one blood vessel chamber disposed between the sink channel and the source channel and including at least one first terminal end in fluid communication with the sink channel and at least one second terminal end in fluid communication with the source channel. Here, at least one blood vessel chamber is arranged to correspond to the thickness and length of a blood vessel to be generated, and arranged to form a blood vessel-generating region by filling a gel and/or an extracellular matrix (ECM).

Figure 10:
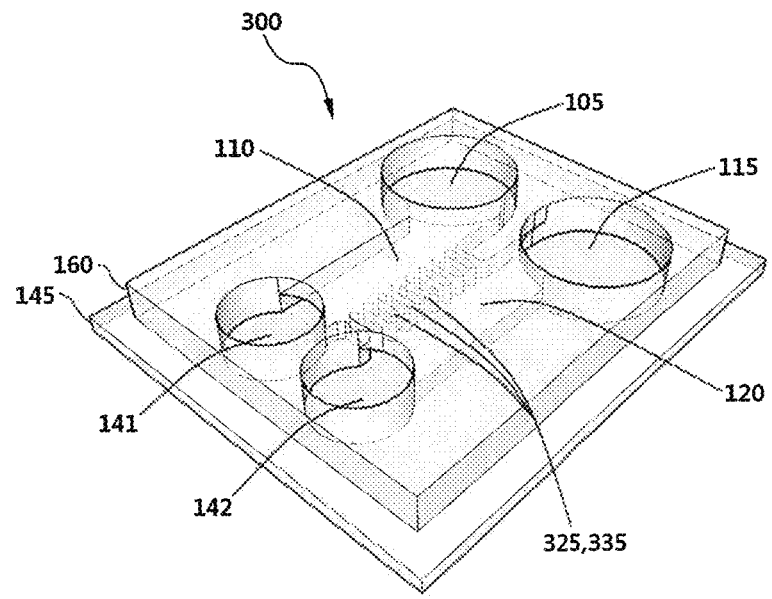
FIG. 10 depicts an embodiment of the blood vessel-generating device.

FIG. 10 depicts an embodiment of the blood vessel-generating device. The blood vessel-generating device 300 includes a base 145 associated with a substrate 160.

The substrate 160 includes a sink inlet 105 in communication with a sink channel 110 capable of injecting fluid into the sink channel 110, and a source inlet 115 in communication with a source channel 120 capable of injecting fluid into the source channel 120. Also, the substrate 160 includes a sink outlet 141 in communication with the sink channel 110 capable of discharging the injected fluid out of the sink channel 110, and a source outlet 142 in communication with the source channel 120 capable of discharging the injected fluid out of the source channel 120. FIG. 10 is a conceptual diagram showing the sink channel 110 and the source channel 120, including an inlet and an outlet. In another embodiment, the sink channel 110 and source channel 120 may form one channel in order to communicate with each other. In this case, the sink inlet 105 and the source inlet 115 may form one inlet, and the sink outlet 141 and the source outlet 142 may form one outlet. Also, it is possible to inject and discharge fluid through the inlets 105 and 115 without using separate outlets 141 and 142.

The sink channel 110 and the source channel 120 provide a passage through which the flow of fluid is allowed. Here, the fluid may include a gel (a fibrin gel, etc.), an ECM, a blood vessel-forming cell (an endothelial cell, an epithelial cell, etc.), a co-culturing cell (an astrocyte, a glial cell, a mesothelial cell, etc.), various angiogenesis factors, a cell culture medium, etc.

In addition, the substrate 160 includes at least one blood vessel chamber 325 disposed between the sink channel 110 and the source channel 120, including at least one first terminal end in fluid communication with the sink channel 110 and at least one second terminal end in fluid communication with the source channel 120. Cross sections of the first and second terminal ends of the at least one blood vessel chamber 325 are configured to correspond to the thickness of a blood vessel to be generated. The length between the first and second terminal ends of at least one blood vessel chamber 325 is configured to correspond to the length of the blood vessel to be generated. That is, a blood vessel-generating region 335 having the thickness and length correspond to the blood vessel to be generated may be formed by filling a gel and/or an ECM into the blood vessel chamber 325, thereby generating one blood vessel in the blood vessel-generating region 335 per each blood vessel chamber 325.

In one specific embodiment of the present invention, the gel may be at least one selected from the group consisting of a collagen gel, a fibrin gel, Matrigel, a self-assembled peptide gel, a polyethylene glycol gel and an alginate gel.

Since the gel and/or the ECM filled into the blood vessel chamber 325 has a predetermined volume, the gel and/or the ECM provides the first and second cell adhesion portions 331 and 332 so that cells can 3-dimensionally attach to the first and second terminal ends adjoining the sink channel 110 and the source channel 120. The gel and/or the ECM also provides a blood vessel-generating region 335 which is a space that may generate a blood vessel by undergoing vascular fusion and angiogenesis processes while the cells are 3-dimensionally proliferated and grown into the gel and/or the ECM. Therefore, the number of the blood vessel chamber 325, the length between the first terminal end and the second terminal end, and the area of a cross section vertical to a longitudinal direction spanning from the first terminal end to the second terminal end may be adjusted to correspond to the number, the length and thickness of the blood vessels to be generated, respectively. Also, the blood vessel chamber 325 may be formed in a straight line as the symmetric gradient chamber 125 in FIG. 1, depending on the shape of the blood vessel to be generated, or may be formed as the asymmetric gradient chambers 130 and 135 in FIG. 1, such that the cross-sections of the first and second terminal ends are different in area. In addition, the plurality of blood vessel chambers 325 may be configured to be in communication with each other according to the blood vessel network to be generated.

Figure 11:
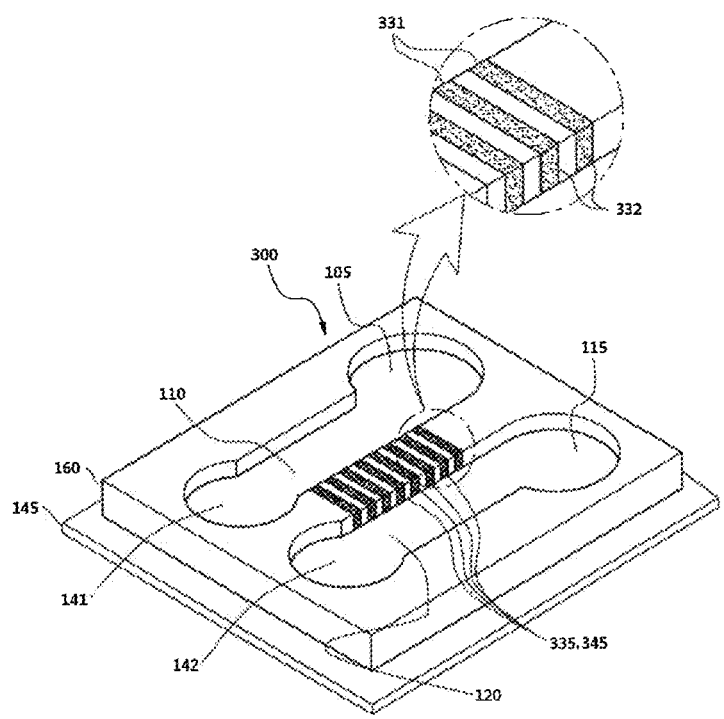
FIG. 11 depicts an embodiment of the blood vessel-generating device of which a gel and/or an ECM is filled into a blood vessel chamber.

FIG. 11 depicts a gel and/or an ECM 345 filled into the blood vessel chamber 325 to form a blood vessel-generating region 335. Unlike FIG. 10 showing that the substrate 160 covers the sink channel 110, the source channel 120 and the blood vessel chamber 325, the blood vessel-generating device 300 shown in FIG. 11 may be used in a state where top surfaces of the sink channel 110, the source channel 120 and the blood vessel chamber 325 are not covered by the substrate 160 but rather are exposed.

Figure 12:
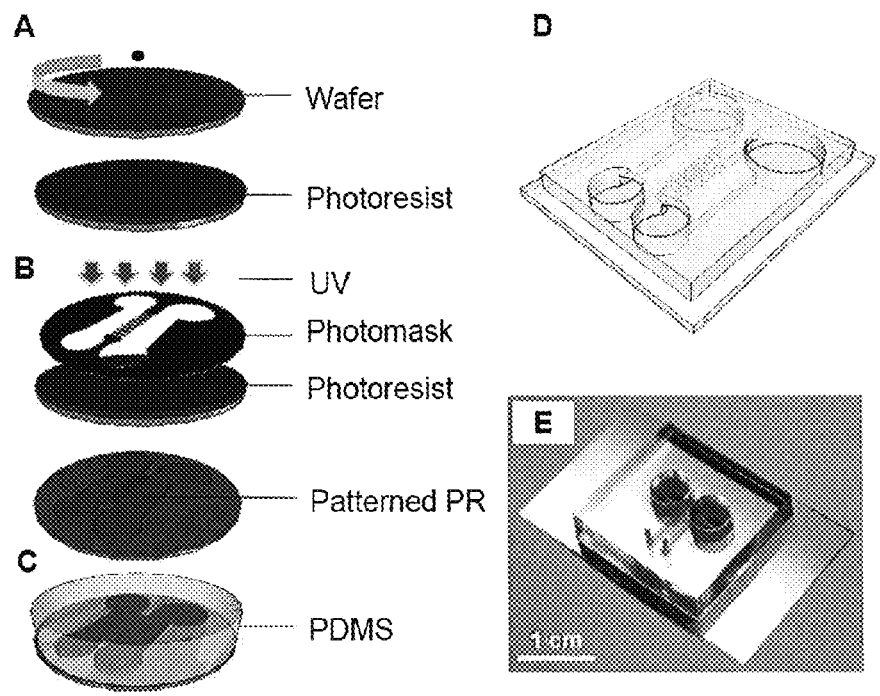
FIG. 12 depicts an embodiment of the process for manufacturing a blood vessel-generating device.

FIG. 12 depicts one example of the process for manufacturing an in vitro blood vessel-generating device according to the present invention. The blood vessel-generating device according to the present invention may be manufactured using a method such as lithography or a molding method, but not limited thereto.

As shown in FIG. 12, a photoresist is first coated on a silicon substrate (A). A negative photoresist, SU-8, in which only a portion irradiated with UV rays is cured may be used as the photoresist. For example, only a portion of the photoresist in which a pattern needs to be formed on the spin-coated photoresist is cured by irradiating the portion of the photoresist with UV rays using a photomask (B). Then, the exposed portion of the photoresist is developed to form patterns corresponding to the sink channel 110, the source channel 120 and the blood vessel chamber 325 on the silicon substrate. A curable material, such as PDMS or polyurethane, used to form a cast is poured into the formed patterns, cured for a certain period of time so that the formed patterns can be formed in the curable material, and then separated from the patterns formed on the silicon substrate (C). The separated cast is subjected to a suitable surface treatment such as plasma treatment, and attached to a slide glass (base) to form a channel (D).

The present invention provides a method of generating a blood vessel including a) filling a gel and/or an ECM into the blood vessel chamber of the blood vessel-generating device; b) injecting a blood vessel-forming cell into the sink channel and/or the source channel of the blood vessel-generating device and attaching the blood vessel-forming cell to the gel and/or the ECM exposed to the first terminal end and the second terminal end of the blood vessel chamber; and c) injecting an angiogenesis factor and a cell culture medium into the sink channel and/or the source channel of the blood vessel-generating device and culturing the blood vessel-forming cell.

Figure 13:
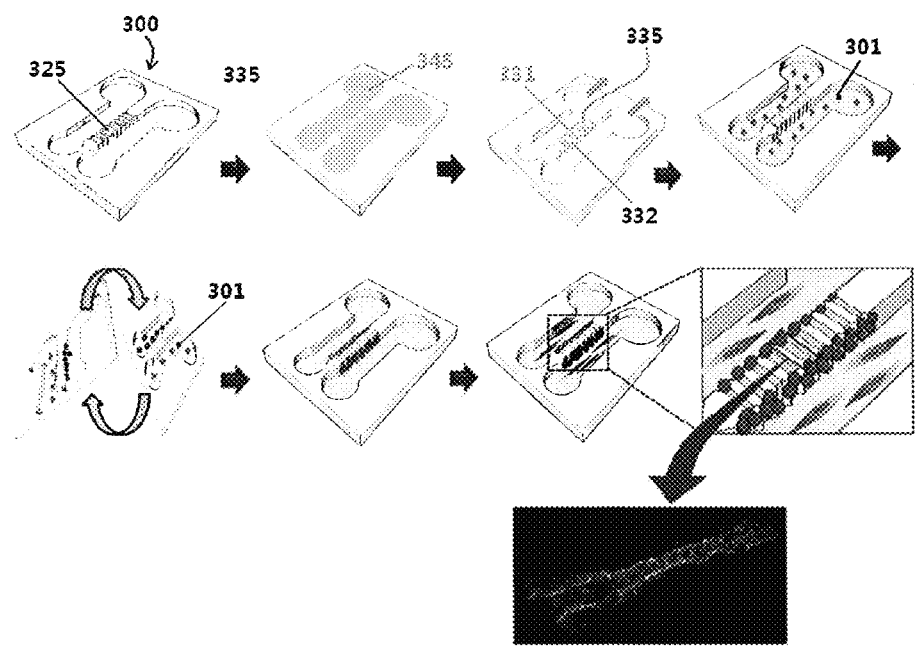
FIG. 13 depicts an embodiment of the process for generating a blood vessel.

FIG. 13 depicts an embodiment of a method of generating a blood vessel using the blood vessel-generating device 300 according to the present invention. As shown in FIG. 13, a gel and/or an ECM is filled into the blood vessel chamber 325 of the blood vessel-generating device 300, and polymerized for a certain period of time to have a predetermined volume. FIG. 13 depicts that the gel and/or the ECM is injected through the sink channel 110 and the source channel 120 of the blood vessel-generating device 300 to be polymerized. The gel and/or the ECM remaining in the sink channel 110 and the source channel 120 is removed via a suction process, thereby allowing the gel and/or the ECM to be filled only into the blood vessel chamber 325. However, this is shown for the purpose of illustrations only. Also the gel and/or the ECM may be filled by simple loading of the gel and/or the ECM as described above, as well as the above-mentioned methods. The gel and/or the ECM may also be filled in the form of a mixture obtained by mixing gel and/or ECM with at least one of a blood vessel-forming cell, an angiogenesis factor, a cell culture medium and a co-culturing cell.

Via the filling step, the gel and/or the ECM having a predetermined volume forms a blood vessel-generating region 335. And the gel and/or the ECM exposed to the first terminal end and the second terminal end of the blood vessel chamber 325 is configured to form first and second cell adhesion portions 331 and 332 which are favorable for the blood vessel-forming cell to attach. Therefore, the blood vessel-forming cell 301 is injected into the sink channel 110 and the source channel 120 of the blood vessel-generating device 300, and attaches to the first terminal end and the second terminal end of the blood vessel chamber 325 as the blood vessel-generating device 300 moves from side to side.

Next, in order to induce proliferation of a blood vessel-forming cell and formation of a blood vessel, an angiogenesis factor and a cell culture medium were injected into the sink channel 110 and the source channel 120 of the blood vessel-generating device 300 and cultured with the blood vessel-forming cell. In order to effectively induce the formation of a blood vessel, a co-culturing cell which interacts with the blood vessel-forming cell and induces the formation of the blood vessel may be injected, and co-cultured. The co-culturing cell may be injected together with an angiogenesis factor and a cell culture medium, or may be injected independently from the angiogenesis factor and the cell culture medium. After this process, the blood vessel may be generated in vitro.

In one specific embodiment of the present invention, the gel may be, for example, at least one selected from a collagen gel, a fibrin gel, Matrigel, a self-assembled peptide gel, a polyethylene glycol gel and an alginate gel. A fibrin gel is used in this embodiment.

In another specific embodiment of the present invention, the blood vessel-forming cell may be, for example, at least one selected from an endothelial cell, an epithelial cell and a cancer cell. The blood vessel-forming cell may be understood to include mutated cells, genetically modified and transfected cells thereof. A human umbilical vain endothelial cell (HUVEC) is used in this embodiment. In the specification, the term "blood vessel-forming cell" refers to a cell that forms a blood vessel by interaction of angiogenesis-inducing agents included in a cell culture medium or angiogenesis factors produced from a co-culturing cell. The blood vessel-forming cell may form a blood vessel through vasculogenesis and angiogenesis that closely mimics the blood vessel forming process observed in vivo. For example, blood vessel endothelial cells, such as HUVEC, a human microvascular endothelial cell, and a human brain microvascular endothelial cell, separated from various human organs may be used as the blood vessel-forming cell. Not only human-derived cell lines, diverse cell lines separated from mouse, rat, cattle, pig may be used as the blood vessel-forming cell. Also, a cancer cell may be used to conduct research on cancer growth and metastasis mechanisms. As described above, the kind of the blood vessel-forming cell may be suitably selected by those skilled in the art according to the purpose of the experiments.

In still another specific embodiment of the present invention, the angiogenesis factor may be, for example, at least one selected from a fibroblast growth factor (FGF), a vascular endothelial growth factor (VEGF), an epidermal growth factor (EGF), a transforming growth factor β (TGTβ), angiopoietins and a sphingosine 1-phosphate (S1P). VEGF is used in this embodiment.

In still another specific embodiment of the present invention, any one of cell culture mediums known in the art may be used as the cell culture medium. An ECM-2 medium (LONZA) is used in this embodiment.

In yet another specific embodiment of the present invention, the co-culturing cell may be a cell that secretes a biochemical material required to form a blood vessel, such as an angiogenesis-inducing agent, through the interaction with the blood vessel-forming cell. The co-culturing cell may be, for example, at least one selected from an astrocyte, a glial cell, a mesothelial cell, a fibroblast, a smooth muscle cell and a cancer cell. The co-culturing cell may be understood to include mutated cells, genetically modified, and transfected cells thereof. When a blood vessel to be generated is a blood vessel in the brain, the co-culturing cell would be preferably an astrocyte, a glial cell, a mesothelial cell or a fibroblast. When a blood vessel to be generated is a blood vessel other than the blood vessel in the brain, the co-culturing cell would be preferably a fibroblast or a smooth muscle cell. Also, in order to conduct research on the relationship between cancer and angiogenesis, a cancer cell may be used as the co-culturing cell. A human lung fibroblast is used in this embodiment.

The addition of the angiogenesis factor, the cell culture medium and the co-culturing cell may be performed to provide a suitable environment for the growth, proliferation and angiogenesis of the blood vessel-forming cell. The kinds and compositions of the angiogenesis factor, the cell culture medium and the co-culturing cell may be suitably selected by those skilled in the art.

Figure 14:
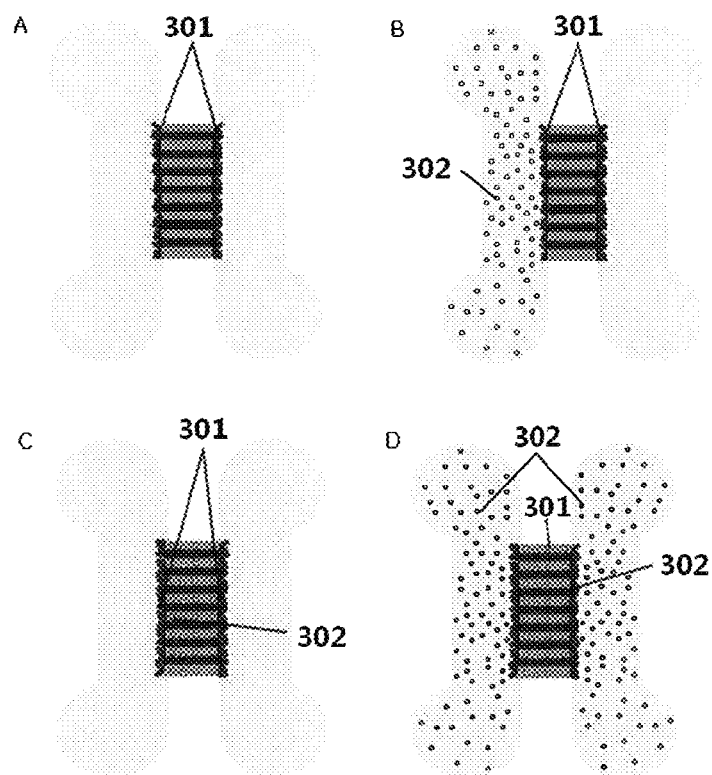
FIG. 14 depicts exemplary states of the blood vessel-generating devices into which a blood vessel-forming cell, an angiogenesis factor and/or co-culturing cell are injected.

FIG. 14 is a conceptual plane view showing various embodiments in which the blood vessel-forming cell 301 is attached to a gel and/or an ECM exposed to the first terminal end and the second terminal end of the blood vessel chamber 325 in the blood vessel-generating device. FIG. 14A shows that the blood vessel-forming cell 301 is attached to the gel and/or the ECM 345 at the first terminal end and the second terminal end of the blood vessel chamber 325. FIG. 14B shows that an angiogenesis factor, a cell culture medium and/or a co-culturing cell 302 are further injected into the sink channel 110 in addition to the attached blood vessel-forming cell 301 of FIG. 14A. FIG. 14C shows that a mixture, obtained by mixing a gel and/or an ECM with an angiogenesis factor, a cell culture medium and/or a co-culturing cell 302, is injected into the blood vessel chamber 325 to form a blood vessel-generating region 335. FIG. 14D shows that an angiogenesis factor, a cell culture medium and/or a co-culturing cell 302 are further injected into the sink channel 110 and the source channel 120, in addition to the injection of the mixture of FIG. 14C.

Figure 15:
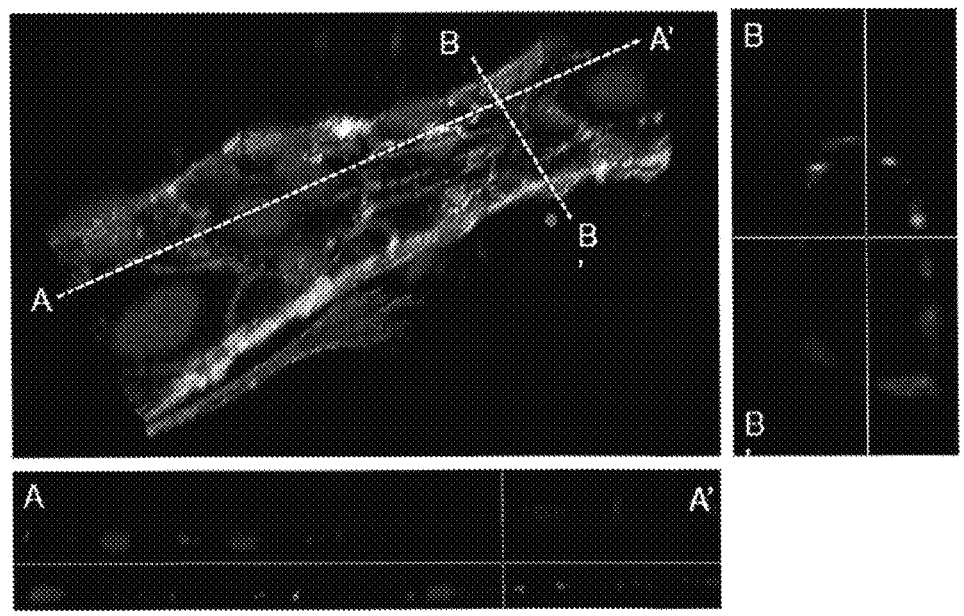
FIG. 15 depicts a microscopic image of a blood vessel generated using the device and the method of generating a blood vessel according to the present invention.

FIG. 15 is a picture showing a blood vessel generated according to the embodiment of FIG. 13, which is stained and observed under a fluorescence microscope. From the microscopic image of the cross sections taken from lines A-A' and B-B', it can be seen that a hollow tubular structure extends in a longitudinal direction to form a blood vessel.

Figure 16:
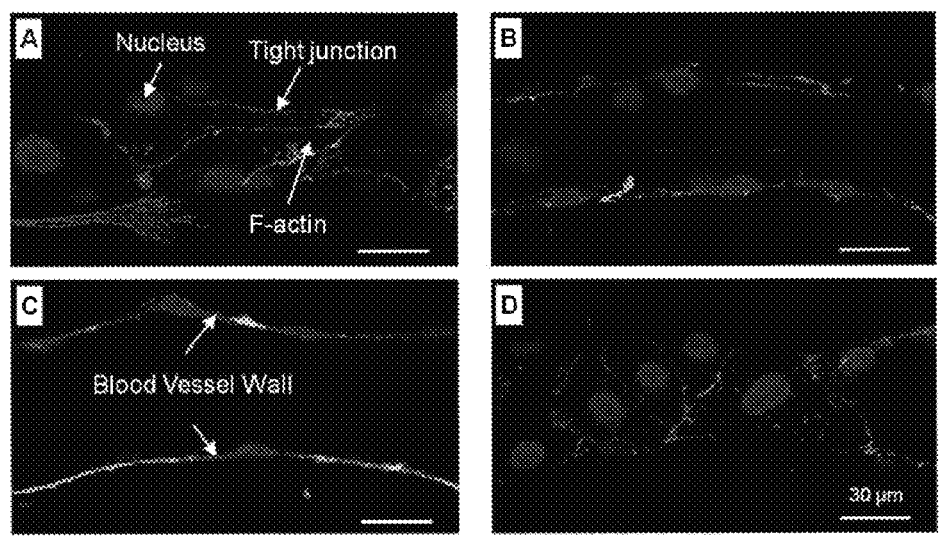
FIG. 16 depicts microscopic images of cross sections (A→D) taken vertically from a lower portion of the blood vessel of FIG. 15 in the Z axis.

FIG. 16 shows a microscopic image of cross-sections (A→D) taken vertically from a lower portion of the blood vessel of FIG. 15 along the Z axis. The blue region represents a nucleus stained with Hoechst 33324, the green region represents F-actin stained with phalloidin, and the red region represents a tight junction stained with ZO-1. From these results, it can be revealed that a tight junction between an endothelial cell and a blood vessel wall is formed to have a structure similar to a real blood vessel.

Still another blood vessel-generating device according to the present invention includes a sink channel in fluid communication with a sink inlet; a source channel in fluid communication with a source inlet substantially parallel to the sink channel; a blood vessel-forming channel in fluid communication a blood vessel-forming channel inlet, disposed in contact with the sides of the sink channel and the source channel between the sink channel and the source channel, substantially parallel to the source channel and the sink channel; a first culture channel in fluid communication with a first culture channel inlet, disposed in contact with the other side of the sink channel, substantially parallel to the sink channel; and a second culture channel in fluid communication with a second culture channel inlet, disposed in contact with the other side of the source channel, substantially parallel to the source channel. Here, a plurality of microstructures configured to allow interaction between biochemical materials included in each channel are arranged in the interfaces of the respective adjacent channels at set intervals.

Figure 17:
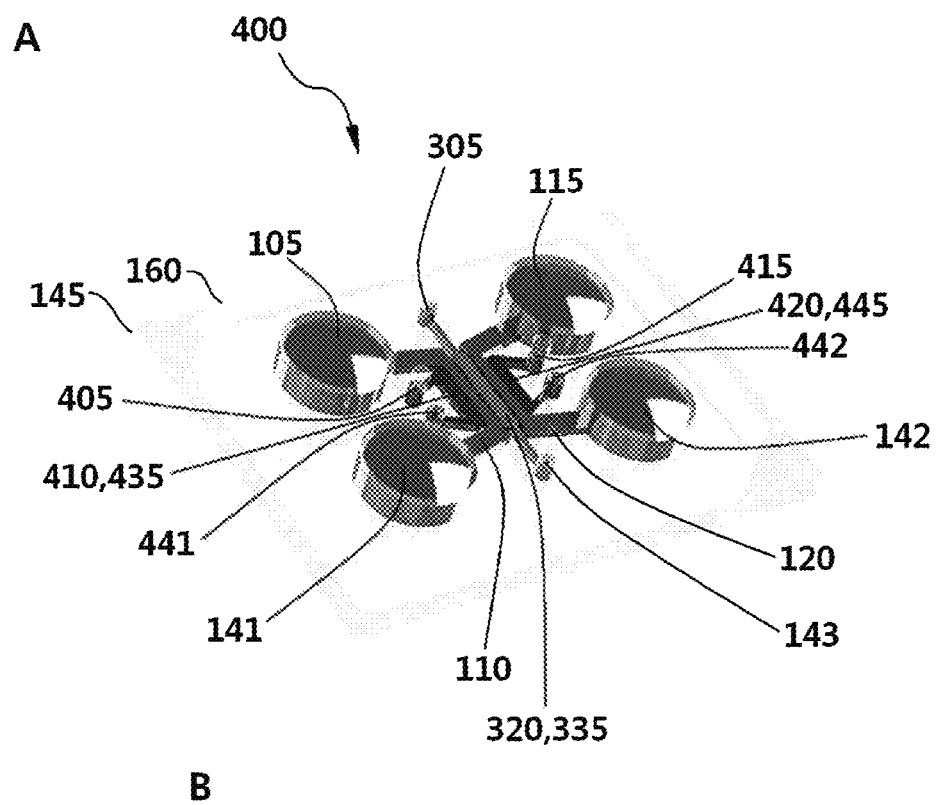
FIG. 17 depicts a second embodiment of the blood vessel-generating device.
Figure 17:
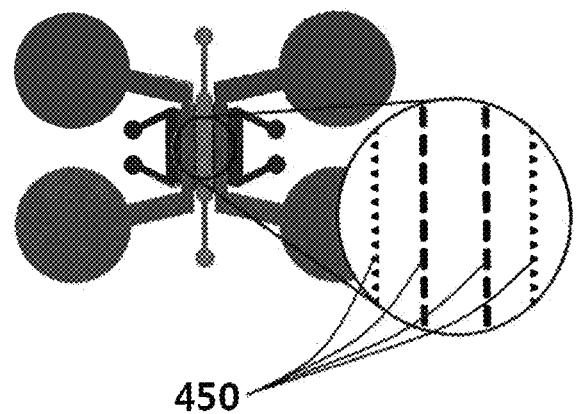

The second embodiment of the blood vessel-generating device is shown in FIG. 17. The blood vessel-generating device 400 includes a base 145 associated with a substrate 160.

The substrate 160 includes a sink inlet 105 in communication with the sink channel 110, capable of injecting fluid into the sink channel 110, and a source inlet 115 in communication with a source channel 120, capable of injecting fluid into the source channel 120. Also, the substrate 160 includes a sink outlet 141 in communication with the sink channel 110, capable of discharging the injected fluid out of the sink channel 110, and a source outlet 142 in communication with the source channel 120, capable of discharging the injected fluid out of the source channel 120. FIG. 17 is a conceptual diagram showing the sink channel 110 and the source channel 120 including an inlet and an outlet. In another embodiment, the sink channel 110 and source channel 120 may form one channel in order to communicate with each other. In this case, the sink inlet 105 and the source inlet 115 may form one inlet, and the sink outlet 141 and the source outlet 142 may form one outlet. Also, it is possible to inject and discharge fluid through the sink inlet 105 and the source inlet 115 without using separate sink and source outlets 141 and 142.

Furthermore, the substrate 160 includes a blood vessel-forming channel 320 disposed in contact with the sides of the sink channel 110 and the source channel 120 between the sink channel 110 and the source channel 120, substantially parallel to the sink channel 110 and the source channel 120. Also, the substrate 160 includes a first culture channel 410 disposed in contact with the other side of the sink channel 110, substantially parallel to the sink channel 110 and a second culture channel 420 disposed in contact with the other side of the source channel 120, substantially parallel to the source channel 120. FIG. 17 is a conceptual diagram showing that each of the blood vessel-forming channel 320 and the first and second culture channels 410 and 420 includes inlets 305, 405 and 415 and outlets 143, 441 and 442. However, it is possible to inject and discharge the fluid through the inlets without using separate outlets.

The adjacent interfaces of the sink channel 110, the source channel 120, the blood vessel-forming channel 320, the first culture channel 410 and the second culture channel 420 are divided by arranging a plurality of microstructures 450 at set intervals so that biochemical materials in each channel can interact with each other. The microstructures 450 have fine column shapes with a length and height ranging from several tens to several hundreds of micrometers (μm). The plurality of microstructures 450 may be arranged at a distance of 500 μM or less. The distance may be suitably determined according to the purpose and conditions of an experiment.

A blood vessel-generating region 335 is 3-dimensionally formed by filling a gel and/or an ECM into the blood vessel-forming channel 320. The blood vessel-generating region 335 provides a space in which blood vessel-forming cells are 3-dimensionally proliferated to form blood vessels. Since the plurality of microstructures 450 are arranged in the adjacent interface between the blood vessel-forming channel 320 and the sink channel 110 and the source channel 120 at set intervals, when a gel and/or an ECM is injected into the blood vessel-forming channel 320, the gel and/or the ECM forms the blood vessel-generating region 325 in the blood vessel-forming channel 320 without any leakage of the gel and/or the ECM between the microstructures 450 due to the surface tension of the gel and/or the ECM. Meanwhile, since various biochemical materials in each channel may flow and diffuse through gaps between the plurality of microstructures 450, various angiogenesis factors and nutrient ingredients included in the sink channel 110 and the source channel 120 may be supplied to the blood vessel-forming channel 320. Also, blood vessels generated in the blood vessel-generating region 335 extend through the gaps formed between the plurality of microstructures 450 to be in communication with the sink channel 110 and the source channel 120, thereby forming an inlet/outlet of the blood vessel and making the blood vessel possible to be perfused with the fluid included in the source channel 120 or the sink channel 110. Therefore, the reaction of the blood vessels may be observed in real time and recorded when directly transferring various biochemical and biophysical materials and signals into the blood vessels through the sink channel 110 and the source channel 120 which are in communication with the gaps between the microstructures 450. Therefore, the number of inlets and outlets of a blood vessel network to be generated may be adjusted by changing the shape, length and number of the microstructures disposed between the blood vessel-forming channel 320 and the sink channel 110 and the source channel 120.

Figure 18:
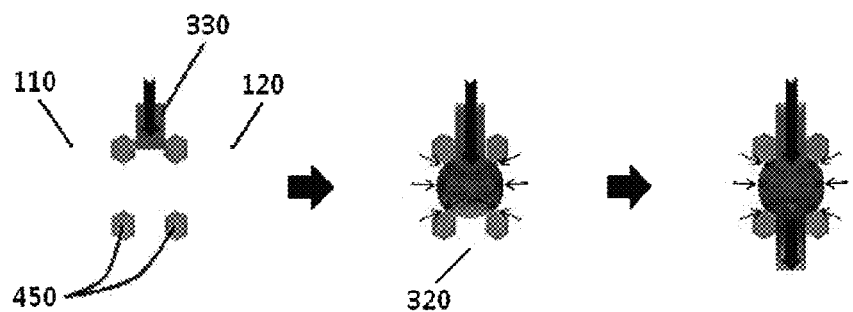
FIG. 18 is a schematic diagram showing a mechanism of filling a gel and/or an ECM into a blood vessel-forming channel of the blood vessel-generating device according to the second embodiment.

FIG. 18 is a schematic diagram showing a mechanism of filling a gel and/or an ECM into a blood vessel-forming channel. According to the present invention, the substrate 160 may be made of a hydrophobic material. An unpolymerized liquid gel and/or ECM 330 injected into the blood vessel-forming channel 320 forms the menisci between the plurality of microstructures 450. In this case, when the pressure inside the liquid menisci are put under a certain level of a pressure (a threshold pressure level), the menisci do not proceed into the sides of the sink channel 110 and the source channel 120 due to the resisting surface tension. A range of the pressure in which the menisci may stop between the microstructures without allowing the menisci to proceed into the sides of the sink channel 110 and the source channel 120 is affected by the gaps between the microstructures and the heights of the microstructures. Therefore, theses two parameters (the gaps between the microstructures and the heights of the microstructures) may be optimized to adjust a threshold pressure level. The specific method of adjusting the threshold pressure level is found in Carlos P. Huang et al. (Engineering microscale cellular niches for three-dimensional multicellular co-cultures, Lab Chip, 2009, 9, 1740-1748). When a gel and/or an ECM is injected into a blood vessel-forming channel, the menisci may be effectively trapped between microstructures by adjusting the gaps between the microstructures and the heights of the microstructures, thereby precisely adjusting the filling of a gel and/or an ECM between channels that are not completely physically separated from each other. This is also applied in the same manner even when a gel and/or an ECM is filled into the first and second culture channels.

Cell culture regions 435 and 445 are 3-dimensionally formed by filling a gel and/or an ECM into the first and second culture channels 410 and 420. Since the plurality of microstructures 450 are arranged in the adjacent interfaces between the first and second culture channels 410 and 420 and the sink channel 110 and the source channel 120 at set intervals, when a gel and/or an ECM is injected into the first and second culture channels 410 and 420, the gel and/or the ECM forms cell culture regions 435 and 445 in the first and second culture channels 410 and 420 without any leakage of the gel and/or the ECM between the microstructures 450 due to the surface tension of the gel and/or the ECM. The cell culture regions 435 and 445 provide a space in which co-culturing cells may be 3-dimensionally proliferated. This 3-dimensional culturing may simulate an in vivo environment more realistically, and thus it is possible to promote production and secretion of various signaling materials of the co-culturing cells. Meanwhile, since the various signaling materials produced in the first and second culture channels 410 and 420 and various biochemical material such as an angiogenesis factor included in the sink channel 110 and the source channel 120 may diffuse through the gaps between the plurality of microstructures 450, it is possible to perform the active interaction of biochemical materials between the first culture channel 410 and the sink channel 110 and between the second culture channel 420 and the source channel 120.

The sink channel 110 and the sink channel 120 provide a passage through which the flow of fluid is allowed. Here, the fluid may include a cell culture medium, a variety of angiogenesis factors, etc. As each of the sink channel 110 and the source channel 120 is disposed between the blood vessel-forming channel 335 and the first and second culture channels 410 and 420, cell culture media and angiogenesis factors are supplied to the blood vessel-forming channel 335 and the first and second culture channels 410 and 420. In this manner, the sink channel 110 and the sink channel 120 provide a passage through which two cell groups (a blood vessel-forming cell and a co-culturing cell) in the blood vessel-forming channel 335 and the first and second culture channels 410 and 420 may interact with each other via paracrine signaling, and the blood vessel-forming cells and the co-culturing cells may be cultured for an extended period of time. Also, since the blood vessel-forming cells and the co-culturing cells are physically separated from each other by the sink channel 110 and the source channel 120, the blood vessel-forming cells and the co-culturing cells may be readily observed and analyzed independently from each other. In particular, since the sink channel 110 and the source channel 120 are in communication with the inlets/outlets of vascular networks formed at gaps between the microstructures 450, it is possible to exert a variety of biochemical and biophysical materials and signals into the blood vessels through the gaps. Therefore, it is possible to simulate the interaction between the variety of biochemical and biophysical signals and the blood vessels, thereby imaging and quantifying the response of the blood vessels to various stimuli in real time.

When the blood vessel-generating device 400 according to the present invention is used to generate a blood vessel, the kinds and characteristics of a gel and/or an ECM, a blood vessel-forming cell, a cell culture medium and a co-culturing cell are the same as described above.

The present invention also provides a method of generating a blood vessel including a) injecting i) a gel and/or an ECM and ii) a blood vessel-forming cell into the blood vessel-forming channel of the blood vessel-generating device; b) injecting i) the gel and/or the ECM and ii) a co-culturing cell into the first culture channel and/or the second culture channel of the blood vessel-generating device; and c) injecting an angiogenesis factor and a cell culture medium into the sink channel and/or the source channel of the blood vessel-generating device and culturing the blood vessel-forming cell and the co-culturing cell. By the present method, a vasculogenesis process can be simulated.

Figure 19:
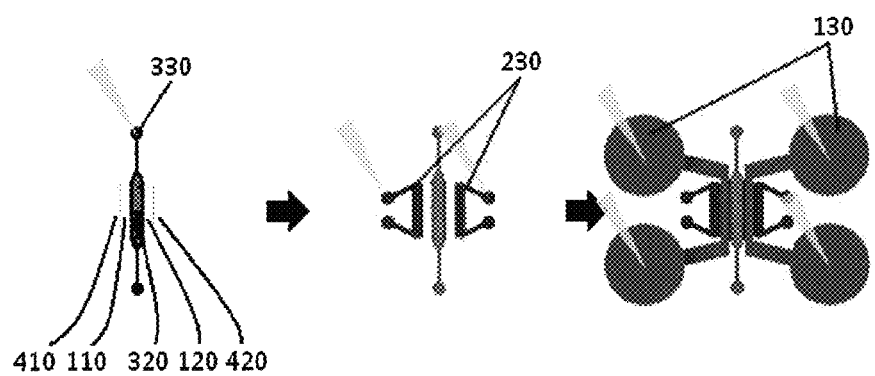
FIG. 19 is a schematic diagram showing some of the methods of generating a blood vessel using the blood vessel-generating device according to the second embodiment.

FIG. 19 depicts a method of generating a blood vessel using the blood vessel-generating device 400 according to the present invention. Here, the method of generating a blood vessel includes injecting a gel and/or an ECM and a blood vessel-forming cell 330 into the blood vessel-forming channel 320, injecting the gel and/or the ECM and a co-culturing cell 230 into the first and second culture channels 410 and 420, and injecting a fluid 130 including a cell culture medium and various angiogenesis factors into the sink channel 110 and the source channel 120. When the gel, the ECM, cells, the cell culture media and the various angiogenesis factors are injected into each channel, additional external experimental equipment is not required, and they may be simply injected using a pipette. Also, the blood vessel-forming cells and the co-culturing cells may be mixed with a gel and/or an ECM to be injected, and may also be injected independently from the gel and/or the ECM through the sink or the source channel to make them adhere on the side wall of gel and/or ECM formed between the microstructures. The method using the blood vessel-forming cells mixed with gel and/or ECM and injected into the blood vessel-forming channel may mimic vasculogenic formation of vessel networks, and the method using the blood vessel-forming cells attached on gel and/or ECM may mimic angiogenesis process allowing formation of angiogenic sprouts and tip cells. FIG. 19 is a conceptual diagram showing that a gel and/or an ECM and a blood vessel-forming cell 330 are injected into the blood vessel-forming channel 320, and then a gel and/or an ECM and a co-culturing cell 230 are injected into the first and second culture channels 410 and 420. However, the injection order does not affect the formation of a blood vessel. Therefore, the order of injecting the materials such as an ECM into each channel may be varied according to the experimenter's convenience and characteristics of experiments. The gel and/or the ECM injected into each channel may be polymerized by increased temperature, chemical reaction or light irradiation, depending on the kind of the gel and/or the ECM. After this polymerizing process, a nutrient ingredient and an angiogenesis factor may be supplied to the blood vessel-forming channel 320 and the first and second culture channels 410 and 420 by injecting a cell culture medium into the sink and source channels. Long-term cell culture and blood vessel formation are possible by inducing paracrine interactions and nutrient factor supply between respective channels.

Figure 20:
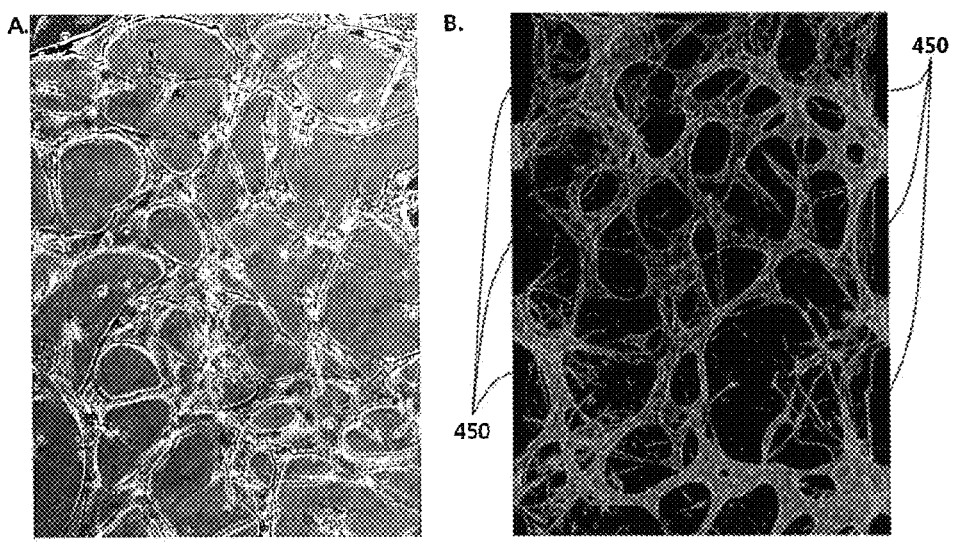
FIG. 20 depicts a microscopic image of a blood vessel network generated by simulating a vasculogenesis process using the device and method for generating a blood vessel according to the present invention.

FIG. 20 is a microscopic image of a blood vessel network formed according to an embodiment of the present invention by injecting a mixture, which was obtained by mixing endothelial cells, HUVECs, and fibroblasts, normal human lung fibroblasts (NHLFs), with fibrin gels, into each of the blood vessel-forming channel 320 and the first and second culture channels 410 and 420; injecting a cell culture medium, endothelial cell growth medium-2 (EGM-2), into the sink channel 110 and the source channel 120; and culturing the cell culture medium. In (B), the blue region represents nucleus stained with Hoechst 33324, the green region represents F-actin stained with phalloidin. From these results, it can be revealed that the blood vessels are interconnected in a complicated pattern, and extend through the gaps formed between the microstructures 450 to be in communication with the cell culture medium in the sink channel 110 and the source channel 120. Therefore, it can be seen that the interior of the blood vessels and a fluid environment of the cell culture medium exist in the form of a continuous phase.

The present invention also provides a method of generating a blood vessel including a) injecting i) a gel and/or an ECM into the blood vessel-forming channel of the blood vessel-generating device; b) injecting a blood vessel-forming cell into the sink channel and/or the source channel of the blood vessel-generating device, and attaching the blood vessel-forming cell to the gel and/or the ECM exposed between the microstructures arranged in the sides of the blood vessel-forming channel; c) injecting i) the gel and/or the ECM and ii) a co-culturing cell into the first culture channel and/or the second culture channel of the blood vessel-generating device; and d) injecting an angiogenesis factor and a cell culture medium into the sink channel and/or the source channel of the blood vessel-generating device and culturing the blood vessel-forming cell and the co-culturing cell. By the present method, an angiogenesis process can be simulated.

Except for injecting the blood vessel-forming cell via the sink channel and/or the source channel and attaching the blood vessel-forming cell to the gel and/or the ECM exposed between the microstructures, the specific method is the same as described above.

Figure 21:
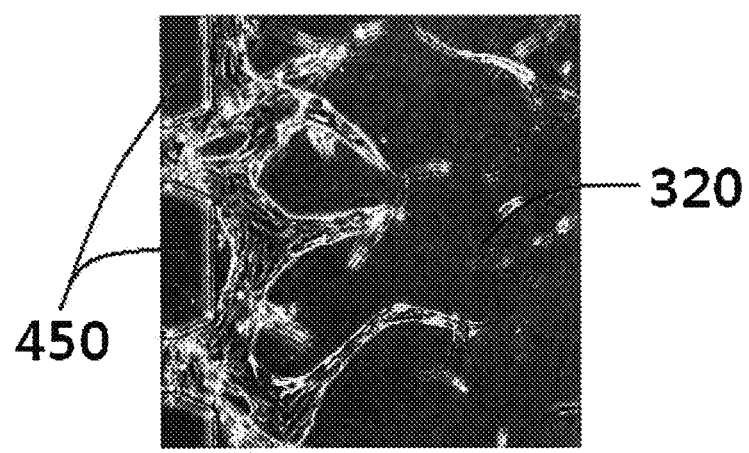
FIG. 21 depicts a picture of another blood vessel network generated by simulating an angiogenesis process using the device and method for generating a blood vessel according to the present invention.

FIG. 21 is a picture showing angiogenic sprouts formed by simulating angiogenesis. Here, the angiogenic sprouts are induced by filling fibrin gels into the blood vessel-forming channel 320 to form a blood vessel-generating region 335; injecting endothelial cells, HUVECs, into the sink channel 110 disposed in the left side of the blood vessel-forming channel 320; attaching the HUVECs to fibrin gels exposed through the gaps between the microstructures 450; and 3-dimensionally culturing fibroblasts, NHLFs, in the second culture channel 420 disposed in the right side of the blood vessel-forming channel 320. In this case, it was revealed that the angiogenic sprouts grew from the left side of the blood vessel-generating region 335 to which the HUVECs are attached to the right side of the blood vessel-generating region 335 in which the fibroblast NHLFs are cultured.

In one specific embodiment of the present invention as described above, the blood vessel-generating device 400 according to the present invention may form a concentration gradient of various signaling materials secreted by the co-culturing cells by adjusting a relative density or by culturing different kinds of cells between the co-culturing cells cultured in the first and second culture channels 410 and 420, disposed respectively on the left and right of the blood vessel-forming channel 320. In addition, the amounts of various signaling materials secreted by the co-culturing cells may be controlled by adjusting a relative density between the co-culturing cells and the blood vessel-forming cells. Also, blood vessel-generating device 400 according to the present invention may also form a concentration gradient of various angiogenesis factors and nutrient ingredients by adjusting a relative flow rate or the kind and concentration of the biochemical materials between the sink channel 110 and the source channel 120, disposed respectively on the left and right sides of the blood vessel-forming channel 320.

According to another specific embodiment of the present invention, blood vessels may be induced to have blood vessel characteristics which appear in specific organs and tissues of the human body, and specific physiological and pathological conditions of the human body by adjusting the origins and kinds of the blood vessel-forming cell, the co-culturing cell and the biochemical factors added to gel, ECM or cell culture medium. For example, when cancer cells are injected with the blood vessel endothelial cells, the permeability of the blood vessel network may be increased in response to the various angiogenic factors and inflammation-inducing factors secreted from the cancer cells. On the contrary, when astrocytes are injected as the co-culturing cell, the permeability of the blood vessel network may be lowered by enhancing the tight cell-cell junctions between the cells constituting blood vessels. Also, a blood vessel network may be endowed with characteristics similar to those of the blood vessels in the brain by co-culturing neuroglial cells in an adjacent external portion of the generated blood vessel. Also, various interactions of the blood vessel-pericyte may be induced by co-culturing a mesenchymal stem cell, thereby realizing a cellular microenvironment in which a variety of research may be performed.

When adjusting permeability of the blood vessel network, the permeability of blood vessels may be measured by introducing a fluorescent dye and quantifying fluorescent intensity of the dye that diffuses across the vessel walls. Also, the permeability may be measured by embedding an electrode at the luminal side of the vessel and the other electrode at the albuminal side of the vessel which allows quantitative measurement of transendothelial electrical resistance (TEER) values across the vessel walls.

In still another specific embodiment of the present invention, an in vitro model may be provided, which may be used to understand cancer growth and the metastasis mechanism by inducing the formation of a blood vessel by a cancer cell, or disposing a cancer cell in or out of a blood vessel. In order for an angiogenesis factor secreted from a cancer cell to simulate a process of inducing morphogenesis or directional growth of blood vessel endothelial cells, the cancer cell may be mixed with a gel and/or an ECM in the first and second culture channels. Also, extravasation or intravasation of cancer cells through the vessel walls can be modeled by introducing cancer cells into the luminal side or the abluminal side of the vessel. In addition, in the above specific embodiment, cells penetrable from the blood stream into a tissue or from the tissue into the blood stream through a blood vessel wall are not limited to cancer cells. Representative examples of other cell groups that move between the tissue and the blood stream through the blood vessel wall include immune cells such as macrophages, neutrophils, etc. According to yet another specific embodiment of the present invention, an interaction between an immune cell and a blood vessel may be simulated by introducing a fluid suspended with these immune cells into the blood vessels.

As described above, the blood vessel, which is formed in the blood vessel-generating region 335 using the blood vessel-generating device 400 according to the present invention, may communicate with the sink channel 110 and the source channel 120 through the gaps formed between the plurality of microstructures 450, as shown in FIG. 20 and FIG. 21. In this case, various biochemical and biophysical stimulations and signals may be directly delivered into the blood vessels generated via the sink channel 100 and the source channel 120, and the response of the blood vessels may be observed and imaged in real time.

According to one specific embodiment of the present invention, a hydrostatic pressure between the sink channel 110 and the source channel 120 may be induced by adjusting the volume of the cell culture medium injected into the sink inlet 105 and/or outlet 141, and the source inlet 115 and/or outlet 142. The difference in the induced hydrostatic pressure enables the cell culture medium to flow into the blood vessel network in communication with the sink channel 110 and the source channel 120 through the gaps formed between the microstructures 450. In this case, morphological and functional characteristics such as the diameter, length, permeability of the blood vessel may be adjusted by mixing the injected fluid with various biochemical materials that may control the characteristics of the blood vessel. Also, a flow rate of the biochemical materials flowing through the blood vessel may be controlled according to the quantitative difference in hydrostatic pressure. Therefore, the response or remodeling of a 3-dimensional blood vessel under a biophysical stimuli induced by a shear stress acting on vessel walls may be imaged and quantified.

Furthermore, a blood stream may be simulated by applying various physiological and pathological levels of blood flow into blood vessels and blood vessel network using a hydrostatic pressure or an external pump. In addition, a blood vessel wall-cell interaction observed during various physiological and pathological physical activities may be simulated at a level similar to an in vivo environment by incorporating a variety of cell groups interacting with the inner walls of blood vessels into the blood stream directed into the blood vessel.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or claims, should be understood to contemplate the possibilities of including one of the terms, either of the terms, or both terms. For example, the phrase "A or B" will be understood to include the possibilities of "A" or "B" or "A and B."

The examples set forth above are provided to give those of ordinary skill in the art a complete disclosure and description of how to make and use the embodiments of the device, systems and methods described herein, and are not intended to limit the scope of the various embodiments thereof. Modifications of the above-described modes for carrying out the device, systems and methods that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of devices, systems and methods have been described. Nevertheless, it will be understood that various modifications may be made without departing from the spirit and scope of such embodiments. Accordingly, other embodiments are within the scope of the following claims.

What is claimed is:

1. A method of generating a blood vessel comprising:
a) injecting i) gel and an extracellular matrix (ECM) and ii) a blood vessel-forming cell into a blood vessel-forming channel of a blood vessel-generating device comprising a) a sink channel in fluid communication with a sink inlet, b) a source channel in fluid communication with a source inlet parallel to the sink channel, c) the blood vessel-forming channel in fluid communication with a blood vessel-forming channel inlet, disposed in contact with the sides of the sink channel and the source channel between the sink channel and the source channel, parallel to the source channel and the sink channel, d) a first culture channel in fluid communication with a first culture channel inlet, disposed in contact with the other side of the sink channel, parallel to the sink channel and e) a second culture channel in fluid communication with a second culture channel inlet, disposed in contact with the other side of the source channel, parallel to the source channel, wherein a plurality of microstructures configured to allow interaction between biochemical materials included in each channel are arranged in interfaces of the respective adjacent channels at set intervals, and wherein the sink channel is disposed between the blood vessel-forming channel and the first culture channel, and the source channel is disposed between the blood vessel-forming channel and the second culture channel;
b) injecting the ECM and a co-culturing cell into the first culture channel and/or the second culture channel of the blood vessel-generating device; and
c) injecting an angiogenesis factor and/or a cell culture medium into the sink channel and/or the source channel of the blood vessel-generating device, and culturing the blood vessel-forming cell and the co-culturing cell; and
d) interacting the blood vessel-forming cell with the co-culturing cell via paracrine signaling.

2. A method of generating a blood vessel comprising:
a) injecting a gel and an extracellular matrix (ECM) into a blood vessel-forming channel of a blood vessel-generating device comprising a) a sink channel in fluid communication with a sink inlet, b) a source channel in fluid communication with a source inlet parallel to the sink channel, c) the blood vessel-forming channel in fluid communication with a blood vessel-forming channel inlet, disposed in contact with the sides of the sink channel and the source channel between the sink channel and the source channel, parallel to the source channel and the sink channel, d) a first culture channel in fluid communication with a first culture channel inlet, disposed in contact with the other side of the sink channel, parallel to the sink channel and e) a second culture channel in fluid communication with a second culture channel inlet, disposed in contact with the other side of the source channel, parallel to the source channel, wherein a plurality of microstructures configured to allow interaction between biochemical materials included in each channel are arranged in interfaces of the respective adjacent channels at set intervals, and wherein the sink channel is disposed between the blood vessel-forming channel and the first culture channel, and the source channel is disposed between the blood vessel-forming channel and the second culture channel;
b) injecting a blood vessel-forming cell into the sink channel and/or the source channel of the blood vessel-generating device, and attaching the blood vessel-forming cell to the gel and/or the ECM exposed between the microstructures arranged in the sides of the blood vessel-forming channel;
c) injecting the ECM and a co-culturing cell into the first culture channel and/or the second culture channel of the blood vessel-generating device; and
d) injecting an angiogenesis factor and a cell culture medium into the sink channel and/or the source channel of the blood vessel-generating device, and culturing the blood vessel-forming cell and the co-culturing cell;
e) interacting the blood vessel-forming cell with the co-culturing cell via paracrine signaling.

3. The method according to claim 1 or 2, wherein the blood vessel-forming cell is at least one selected from the group consisting of an endothelial cell, an epithelial cell and a cancer cell.

4. The method according to claim 1 or 2, wherein the gel is at least one selected from the group consisting of a collagen gel, a fibrin gel, a self-assembled peptide gel, a polyethylene glycol gel and an alginate gel.

5. The method according to claim 1 or 2, wherein the co-culturing cell is at least one selected from the group consisting of an astrocyte, a glial cell, a mesothelial cell, a fibroblast, a smooth muscle cell and a cancer cell.

* * * * *